US011617621B2

(12) United States Patent
Daniels et al.

(10) Patent No.: US 11,617,621 B2
(45) Date of Patent: Apr. 4, 2023

(54) SYSTEM AND METHOD FOR MULTI-PROBE GUIDANCE

(71) Applicant: Canon U.S.A., Inc., Melville, NY (US)

(72) Inventors: Barret Daniels, Cambridge, MA (US); Jacob Schieffelin Brauer, Cambridge, MA (US); Antonio Bonillas Vaca, Boston, MA (US); Derek John Hugger, Mont Vernon, NH (US); John E. Longan, Nashua, NH (US); Christopher Wayne Thurrott, Townsend, MA (US)

(73) Assignee: Canon U.S.A., Inc., Melville, NY (US)

( * ) Notice: Subject to any disclaimer, the term of this patent is extended or adjusted under 35 U.S.C. 154(b) by 906 days.

(21) Appl. No.: 16/527,919

(22) Filed: Jul. 31, 2019

(65) Prior Publication Data
US 2020/0038110 A1    Feb. 6, 2020

Related U.S. Application Data

(60) Provisional application No. 62/871,556, filed on Jul. 8, 2019, provisional application No. 62/714,566, filed on Aug. 3, 2018.

(51) Int. Cl.
*A61B 34/10* (2016.01)
*A61B 10/04* (2006.01)
(Continued)

(52) U.S. Cl.
CPC .............. *A61B 34/10* (2016.02); *A61B 10/04* (2013.01); *A61B 18/082* (2013.01);
(Continued)

(58) Field of Classification Search
CPC ....... A61B 10/04; A61B 18/02; A61B 18/082; A61B 18/1477; A61B 18/1815;
(Continued)

(56) References Cited

U.S. PATENT DOCUMENTS

| 5,196,019 A | 3/1993 | Davis et al. |
| 6,487,431 B1 | 11/2002 | Iwano et al. |

(Continued)

FOREIGN PATENT DOCUMENTS

| DE | 29821464 U1 | 9/1999 |
| JP | 2005-536278 A | 12/2005 |

(Continued)

*Primary Examiner* — Sing-Wai Wu
(74) *Attorney, Agent, or Firm* — Canon U.S.A., Inc., IP Division

(57) ABSTRACT

A system and method for supporting multi-probe guidance are disclosed. The system comprises: a medical guidance apparatus comprising: a rotatable portion which is rotatable around a first axis; an arc guide attached to or integrally formed with the rotatable portion, and a probe holder movably mounted on the arc guide. The probe holder is rotatable around a second axis perpendicular to the first axis by being translated along an arcuate path defined by the shape of the arc guide. In one embodiment, the probe holder includes a plurality of probe channels to guide a corresponding plurality of probes parallel to each other towards a subject. In other embodiment, the probe holder includes a single probe channel which is offset from a center point of the guidance apparatus by a fixed distance such that each probe can be inserted sequentially through a different insertion point without colliding at the center point.

18 Claims, 10 Drawing Sheets

(51) Int. Cl.
*A61B 18/08* (2006.01)
*G16H 30/20* (2018.01)
*A61B 18/02* (2006.01)
*G06T 19/00* (2011.01)
*A61B 18/14* (2006.01)
*A61B 90/00* (2016.01)
*G06T 7/00* (2017.01)
*A61B 18/18* (2006.01)
*G06T 15/08* (2011.01)
*A61B 18/00* (2006.01)

(52) U.S. Cl.
CPC ........... *G06T 7/0012* (2013.01); *G16H 30/20* (2018.01); *A61B 18/1815* (2013.01); *A61B 2010/045* (2013.01); *A61B 2018/00577* (2013.01); *A61B 2034/104* (2016.02); *A61B 2034/107* (2016.02); *G06T 15/08* (2013.01); *G06T 19/00* (2013.01); *G06T 2207/20104* (2013.01); *G06T 2207/20108* (2013.01); *G06T 2210/41* (2013.01)

(58) Field of Classification Search
CPC ...... A61B 2010/045; A61B 2018/0022; A61B 34/10; A61B 2018/0025; A61B 2018/00577; A61B 2018/0293; A61B 2034/104; A61B 2034/107; A61B 2034/2059; A61B 2090/0811; A61B 2090/374; A61B 2090/3762; A61B 2090/378; A61B 2090/3937; A61B 2090/3983; A61B 34/25; A61B 90/11; G06T 15/08; G06T 19/00; G06T 2207/20104; G06T 2207/20108; G06T 2210/41; G06T 7/0012; G16H 20/40; G16H 30/20; G16H 30/40
See application file for complete search history.

(56) References Cited

U.S. PATENT DOCUMENTS

| | | | |
|---|---|---|---|
| 6,505,065 | B1 | 1/2003 | Yanof et al. |
| 8,511,316 | B2 | 8/2013 | Boese et al. |
| 9,125,676 | B2 | 9/2015 | Sahni |
| 9,222,996 | B2 | 12/2015 | Fujimoto et al. |
| 9,408,627 | B2 | 8/2016 | Sahni |
| 9,433,390 | B2 | 9/2016 | Nathaniel et al. |
| 9,867,673 | B2 | 1/2018 | Onuma et al. |
| 2002/0052610 | A1 | 5/2002 | Skakoon et al. |
| 2004/0039429 | A1 | 2/2004 | Daniel et al. |
| 2004/0260312 | A1 | 12/2004 | Magnusson et al. |
| 2006/0229641 | A1 | 10/2006 | Gupta et al. |
| 2008/0200798 | A1 | 8/2008 | Eklund et al. |
| 2010/0063496 | A1 | 3/2010 | Trovato et al. |
| 2010/0082040 | A1 | 4/2010 | Sahni |
| 2010/0228251 | A1 | 9/2010 | Horlle |
| 2012/0022368 | A1 | 1/2012 | Brabrand et al. |
| 2013/0319680 | A1 | 12/2013 | Wishahy |
| 2014/0022245 | A1 | 1/2014 | Brannan et al. |
| 2016/0008074 | A1 | 1/2016 | Glossop |
| 2016/0038247 | A1 | 2/2016 | Bharadwaj et al. |
| 2017/0014200 | A1 | 1/2017 | Onuma et al. |
| 2017/0049503 | A1 | 2/2017 | Cosman et al. |
| 2018/0155970 | A1* | 6/2018 | Krumbiegel .......... E05D 11/087 |
| 2018/0228568 | A1 | 8/2018 | Kato et al. |
| 2019/0105109 | A1 | 8/2019 | Kato |

FOREIGN PATENT DOCUMENTS

| | | |
|---|---|---|
| JP | 2015-047303 A | 3/2015 |
| WO | 2010/096149 A2 | 8/2010 |

* cited by examiner

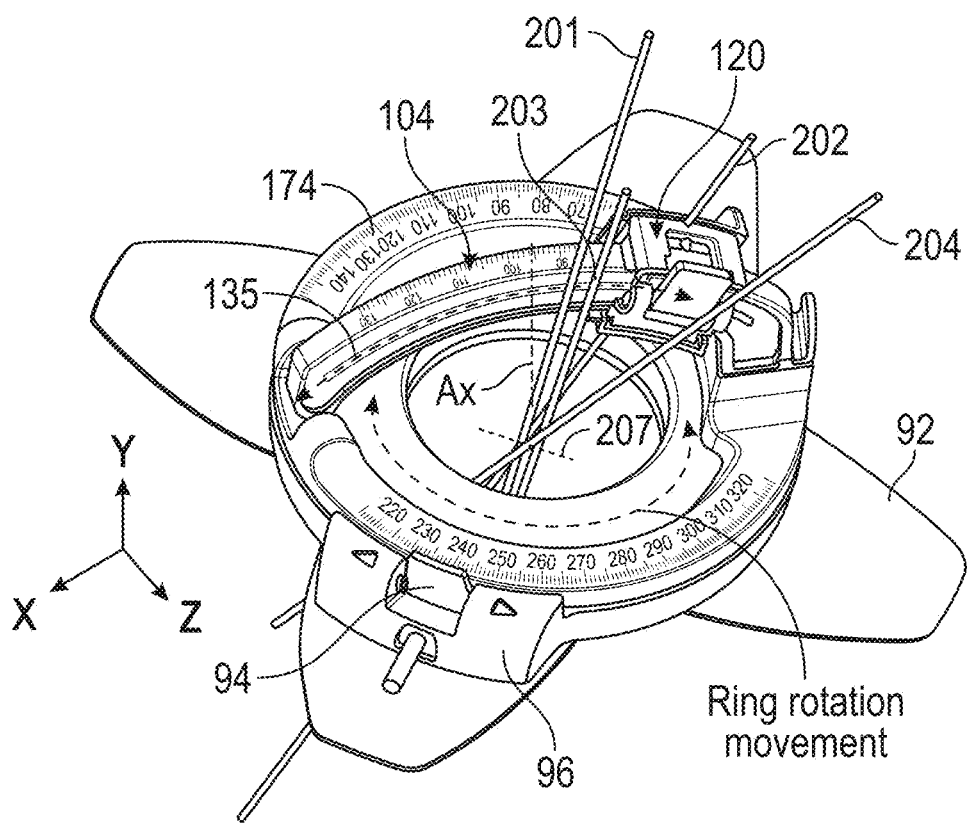
FIG. 2A
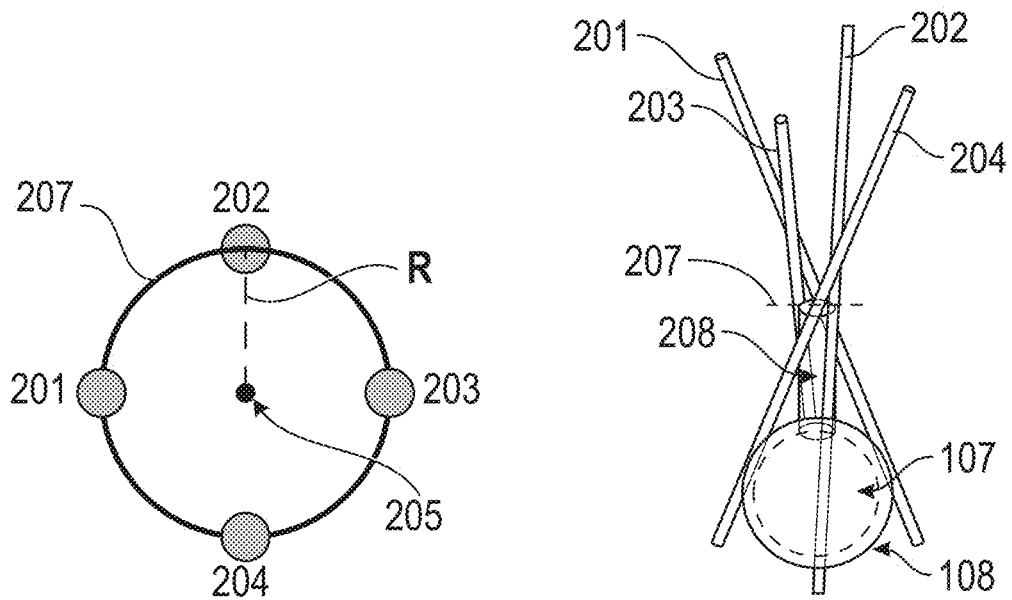
FIG. 2B  FIG. 2C

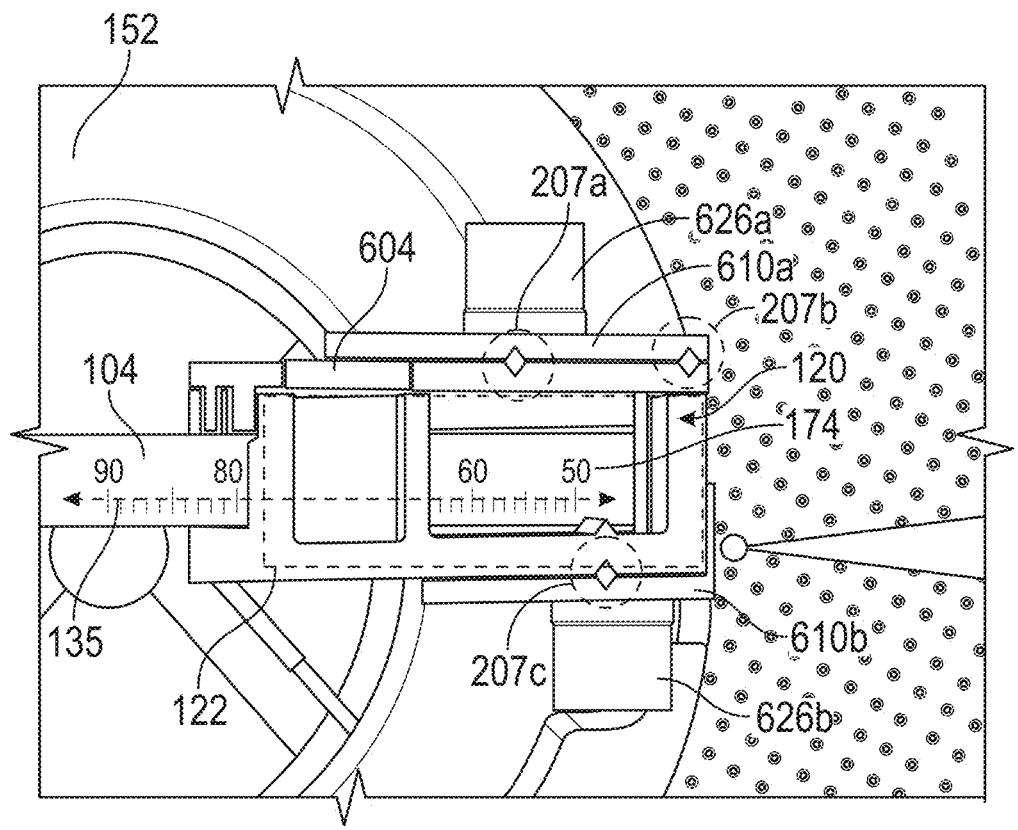
FIG. 3A
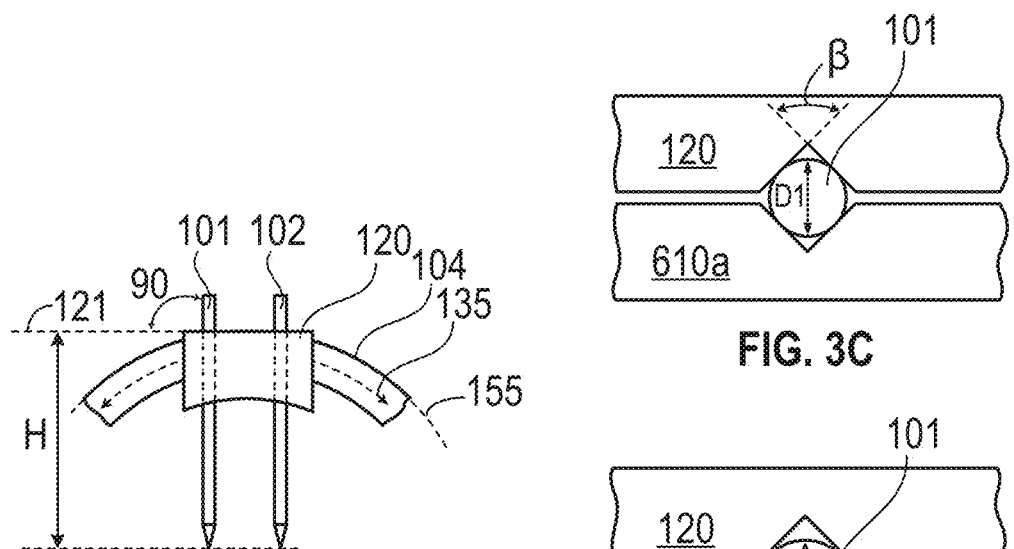
FIG. 3B
FIG. 3C
FIG. 3D

SYSTEM AND METHOD FOR MULTI-PROBE GUIDANCE

CROSS-REFERENCE TO RELATED APPLICATIONS

The present application claims priority to U.S. provisional application 62/714,566 filed Aug. 3, 2018 and U.S. provisional application 62/871,556 filed Jul. 8, 2019, the disclosures of which are incorporated by reference herein in their entirety.

FIELD OF DISCLOSURE

The present disclosure relates generally to the field of medical imaging, such as, but not limited to, the field of interventional oncology, and more particularly to apparatuses, systems, methods and storage media for guidance of multiple ablation probes or biopsy needles. Examples of ablation applications include imaging, identification, evaluation, and/or characterization of biological organs or tissue, such as, but not limited to, identification, location and treatment of lesions or tumors. The present disclosure also relates to an apparatus and method for positioning of one or more needles in a puncture treatment.

BACKGROUND OF THE DISCLOSURE

Minimally invasive medical procedures are becoming increasingly prevalent in the medical community due to shortened hospital stays and improved quality of life for the patient. For example, in the field of interventional oncology, percutaneous ablations are often preferred over surgical resection due to the minimally invasive nature of the procedure and thus shortened patient recovery period.

There are various forms of ablation and biopsy procedures. Successful outcome of these type of procedures requires good planning and careful navigation of the medical instrument to area of interest. Ablation is normally ordered after diagnosis by oncologists who decide that ablation is the best procedure to treat a lesion or tumor. An interventional radiologist (IR) may be involved to gather and analyze images to accurately characterize tumors and their size and to review results from a biopsy procedure. However, diagnostic imaging is rarely good enough to plan with, so an IR may conduct initial imaging before developing/finalizing an action plan and starting an ablation procedure. The ablation strategy may include selection of an imaging modality in the procedure, probe insertion points, a number of probes and trajectories of the insertion, a modality of ablation such as microwave, cryo, etc., patient position during the procedure, coordinating with other clinicians (e.g., anesthetist, nurses, equipment technicians, etc.), etc.

Ablation takes a lot of planning, and there are a lot of variables. For example, clinicians in ablation planning try to figure out where is the target ablation zone including a lesion/tumor, where are the critical structures/features that must be avoided during the procedure, where is the target point in the target zone, what is the entry point on the body surface so that the probe can get into the body and reach a target point(s), what is the trajectory to connect an entry point to a target point while avoiding any critical structure/feature with consideration of needle orientation when scanning the body with the needle inserted, how many probes are needed to form an ablation zone, how big and what shape the ablation zone is, etc. When a lesion/tumor is identified and an ablation zone is defined, based on ablation probe type and quantities, clinicians normally use a visual overlay of the two zones to estimate the coverage zone, which tends to be inaccurate or be a less objective measure since it is a mental visual estimate.

Even though ablation procedures are very complex, the procedure that is currently performed by clinicians is predominantly done manually and iteratively, which is error prone and may increase the time required to perform an ablation (i.e., it is inefficient). Planning in particular is largely performed by clinicians with some help from basic visualization software. Clinicians typically start with reading Computed Tomography (CT) or Magnetic Resonance Imaging (MRI) scans, identify the target region and plan the insertion point and/or trajectory/orientation. For example, in at least one ablation planning scenario, clinicians load Digital Imaging and Communications in Medicine (DICOM) images of a patient into a computer and view 2D slice by slice of the CT or MRI scans of the patient. By going through the DICOM image slices, a clinician may construct a mental 3D model of internal anatomy of concern. By using the DICOM images, the clinicians may identify where the lesion/tumor is and may identify the relationship of the lesion/tumor and its surrounding critical structure, to determine the optimal probe entry point, target point and consequently the trajectory from the entry point to the target point.

Then the clinicians may identify the entry point on the surface of the body that corresponds to what the clinicians envisioned in the image scans. The clinicians may perform a test drive to insert a needle a little bit, perform a scan, and find the difference between the actual needle insertion demonstrated by the scan and what was expected before the insertion. This gives the clinicians a chance to make any correction if necessary. This step may be repeated several times for the needle to finally reach the target point.

Percutaneous ablation procedures require the physician to guide one or more than one ablation probes to the tumor or lesion deep in the body with the aid of medical imaging (e.g. CT, MRI, Ultrasound, etc.). Various ablation modalities exist (radiofrequency, microwave, cryo, laser, and irreversible electroporation). The physician must select the probe which will fully ablate the tumor along with a safety margin surrounding the tumor to reduce the risk of tumor recurrence. In many cases, a single probe cannot achieve full tumor coverage and thus multiple probes are used for a larger ablation zone to ensure full tumor coverage. Moreover, there is often a preset probe configuration that is desired in each ablation modality. For example, in microwave and irreversible electroporation a parallel probe configuration is desired. The probes need to be guided parallel at a preset maximum distance. The preset maximum distance ensures a larger uniform ablation zone. Exceeding the maximum probe distance will result in independent ablation zones around each probe and thus lead to missed tumor cells between probes causing tumor recurrence. In cryo-ablation, many physicians prefer to bracket the tumor in a conical probe arrangement in order to ensure all insertion points of the probes are in close proximity. Sharing a close insertion point for all probes in cryo-ablation is desired so that the physician can more easily protect the skin from cryo burns by applying warm saline around the probe insertion points. In current practice, ablation probes are guided in a free-handed manner using medical imaging for guidance. It is very difficult to achieve these preset probe configurations with this manual approach and thus an improved guidance method is needed.

More specifically, a target point is typically in a center of the lesion or tumor area in a case where a single probe is used. Clinicians may use a pointing device such as a mouse or touch point to mark a location in the center of the lesion/tumor which is shown in the basic visualization software. Clinicians may either place a probe tip to allow ablation to occur, or may implant seeds for radio/chemo therapy. Even the marking process is manual and approximate in nature. In 2D, marking a center position for an object may not be hard, even though many times it may not be accurate due to human visual and motor action inaccuracy/error. However, a clinician using 2D slice view to figure out a center of a 3D volume which includes a stack of 2D slices may be difficult and error prone if the center of the volume is the target point. In addition, the clinician may be tricked by image artifacts and/or human limitation in 3D reasoning. In 3D, marking a center position is much harder because of the intricate limitation of visualization/rendering software. Relying on clinicians' intuition, experience and visual understanding to define a target point is not optimal (for reliability, repeatability, traceability, etc.), particularly in 3D space. When the lesion/tumor has a very complicated shape, defining an appropriate target is more or less an art, and it is difficult to achieve consistency.

If multiple needles are needed to make the ablation zone large enough to cover the target zone, clinicians typically use a first needle as reference, and plan the next needles based on the result from the first or previous needle insertion and/or ablation. If there are multiple needle insertions needed, cases are done mostly in an incremental fashion—for example, plan, insert a needle, scan, make an adjustment or modification to the original plan (if needed) based on the scan of the inserted needle, insert another needle, etc.

In various instances, human intervention and adjustment must be done during the procedure. Tools that currently exist to help clinicians in ablation planning/performance are not adequate. For example, interchangeable probe guides have the issue of the cumbersome nature of changing probe guides with each subsequent needle. Moreover, it is difficult to maintain sterility when there are multiple small interchangeable parts needed to achieve multiple needed insertions. Also, if an angled probe guide is steep enough and the probe guide is rotated around the $2^{nd}$ rotation axis (Z) towards the end of the arc, the inserted needle will collide with a structure (such as a ring) of the device. Also for each probe guide, a user may have to set the probe guide to some predetermined angle or translation for each probe, which is a process that can be very error prone, cumbersome for the user, and difficult to mechanically design with stability to support an inserted probe. Devices/hardware is also lacking to help clinicians aid in the insertion of multiple probes during a procedure.

In current practice, as aforementioned, ablation probes are guided in a free-handed manner using medical imaging for guidance. It is very difficult to achieve these preset probe configurations with this approach and thus an improved guidance method is needed. Prior/current methods related to ablation planning/performance assume no occurrence of organ movement and deformation, either implicitly or explicitly. Clinicians employ incremental insertion movement by trial and error to deal with the inevitable organ movement and deformation (e.g., as aforementioned, a clinician may insert a needle a little, scan, read the image(s) to find out how much the needle is off, adjust or change the needle trajectory if needed or keep going, if the target point is moved during probe insertion, etc.). Currently, a first probe insertion is made and scanned to use the scan as a reference. Then subsequent incremental insertions of the probe may be made towards the target with scans after each insertion to assess same. Such a process may include repositioning the patient if needed to make insertion more controllable. Additionally, an IR or clinician may assume the probe is rigid and that organs have no deformation and movement from now until the insertion. Alternatively to scanning, an ultrasound transducer along with the ablation probe may be used to guide the probe into the planning direction to reach the target, which requires ultrasound image fusion with CT/MRI (CT fluoroscopy is another technique that may be used with CT during planning and performance of ablation). This not only increases the procedure time, but also wastes a lot of efforts in adjustment/making changes. Of course, it is also likely having impact(s) on or causing possible damage to nearby structure and tissues. Considering organ movement and deformation may make ablation planning and performance more complex, and may hamper interaction between clinicians and ablation planning and performance devices. The reality is that many factors (e.g., breathing, body movement or pose change, organ deformation due to interaction with the probe, etc.) affect probe insertion and may change between planned insertion and actual insertion. Such changes may also invalidate the planned insertion. Respiratory gating or asking patients to hold their breath are time consuming monitoring techniques that may be used to assist with insertion. Modeling organ deformation is another way to try to anticipate movement and deformation issues with insertion. However, such procedures do not guarantee success or efficiency.

U.S. Pat. No. 9,867,673 (disclosed by an applicant of the present disclosure) provides a medical support device comprising a first rotational element having a first rotation axis and a first rotational degree of freedom; a second rotational element having a second rotation axis and a second rotational axis and a second degree of freedom that is attached to the first rotational element wherein the second rotational element is configured to guide the direction of one or more needles using a needle guide. The needle guide portion guides a first needle through a first puncture site and a second needle through a second puncture site by adjusting or reconfiguring the needle guide between subsequent needle insertions.

The adjustable probe guide with at least 1 additional degree of freedom disclosed in U.S. Pat. No. 9,867,673 has a limitation that the user must sequentially set the probe guide to some predetermined angle or translation for guiding each probe. This patent also does not disclose a method to achieve accurate parallel probe guidance with a configuration at a preset distance which is desirable for both microwave and irreversible electroporation.

In view of the above, there is a need for software and/or hardware to provide clinicians with help to make ablation easier, more efficient (e.g., reduce procedure time) and more effective (including, but not limited to, more cost-effective (cheaper), optimized for lesion/tumor removal, etc.), in addition to providing enhancement in visualization and/or needle or probe guidance/placement. There is also a need for a reliable and simple ablation apparatus, method and storage medium for guidance of multiple ablation probes that provides a better, faster and more objective way to guide needles and/or probes in configurations necessary for performing ablation.

SUMMARY OF THE INVENTION

One or more systems, devices, methods and storage media are provided herein, for supporting multi-probe treatment of a subject by guiding multiple ablation probes or multiple biopsy needles or a plurality of other needle-like instruments into an area of interest within the subject.

One or more embodiments of the present disclosure relate to one or more medical devices, methods and storage mediums for holding and positioning multiple ablation probes in desired geometric configurations. One or more embodiments provide useful hardware for physically guiding planned needles along planned insertion trajectories.

In one or more embodiments, percutaneous ablation procedures involve the physician having to guide ablation probe(s) to the tumor deep in the body with the aid of medical imaging (e.g. CT, MRI, Ultrasound, etc.). Various ablation modalities exist (radiofrequency, microwave, cryo, laser, and irreversible electroporation). The physician selects the probe which will fully ablate the tumor along with a safety margin surrounding the tumor to reduce the risk of tumor recurrence. In many cases, a single probe cannot achieve full tumor coverage, and thus multiple probes are used for a larger ablation zone to ensure full tumor coverage. Moreover, there is often a preset probe configuration that is desired in each ablation modality. For example, in microwave and irreversible electroporation a parallel probe configuration is desired. In the parallel probe configuration, probes are guided parallel at a preset maximum distance. The preset maximum distance ensures a larger uniform ablation zone. Exceeding the maximum probe distance may result in independent ablation zones around each probe and thus lead to missed tumor cells between probes causing or leading to tumor recurrence. In cryo-ablation, many physicians prefer to bracket the tumor in a conical probe arrangement in order to ensure all insertion points of the probes are in close proximity. Sharing a close insertion point for all probes in cryo-ablation is desired so that the physician can more easily protect the skin from cryo burns by applying warm saline around the probe insertion points.

The present disclosure, via one or more embodiments, achieves fundamental multi-probe configurations desired for ablations (parallel for microwave and irreversible electroporation and conical for cryo) without multiple interchangeable probe guides. One or more embodiments also achieve the fundamental multi-probe configurations by only using two degrees of freedom (see e.g., rotatable portion 100 and probe guide 102 translation along the arc 104 as discussed further below) instead of adding additional degree(s) of freedom (which avoids any related mechanisms for achieving such additional degrees of freedom that likely add stability issues when holding probes along set trajectories). One or more embodiments may achieve parallel and conical probe configurations without the need for interchangeable probe guides or adding an additional degree of freedom to the probe guide. Parallel probe spacing may be controlled to be below a preset maximum with device design to ensure a single uniform ablation zone with multiple probes.

One or more embodiments discussed herein may be combined to achieve irregular probe configurations. In one or more embodiments, the parallel probe distance may be pre-defined by the design of the device (rather than through the user adjusting the device), which eliminates the risk of the user spacing the probes a distance greater than the manufacturer recommended distance. One or more other features discussed herein may reduce the risk of user error.

In accordance with one or more embodiments of the present disclosure, ablation planning and performance apparatuses and systems, and methods and storage mediums may operate to characterize biological objects, such as, but not limited to, lesions, tumors, critical structures, etc.

In accordance with at least another aspect of the present disclosure, the ablation probe placement/guidance technique(s) discussed herein may be employed to reduce the cost of at least one of manufacture and maintenance of ablation planning and performance devices, systems and storage mediums by reducing or minimizing a number of components therein to cut down cost.

According to other aspects of the present disclosure, one or more additional apparatuses, one or more systems, one or more methods, and one or more storage mediums using multiple ablation probe guidance technique(s) are discussed herein. Further features of the present disclosure will become apparent from the following description of exemplary embodiments with reference to the attached drawings.

BRIEF DESCRIPTION OF THE DRAWINGS

For the purposes of illustrating various aspects of the disclosure, wherein like numerals indicate like elements, there are shown in the drawings simplified forms that may be employed, it being understood, however, that the disclosure is not limited by or to the precise arrangements and instrumentalities shown. To assist those of ordinary skill in the relevant art in making and using the subject matter hereof, reference is made to the appended drawings and figures, wherein:

FIGS. 2A-2C are schematic diagrams showing another embodiment of a device and/or system for performing multiple ablation probe guidance in accordance with one or more aspects of the present disclosure;

FIG. 3A is a top down view of an exemplary probe holder; FIG. 3B shows a side view of the probe holder configured to guide multiple probes parallel to each other; FIG. 3C and FIG. 3D both show a top down view of a guide channel configured to receive therein needle-like instruments of a plurality of sizes;

DETAILED DESCRIPTION

Figure 1A:
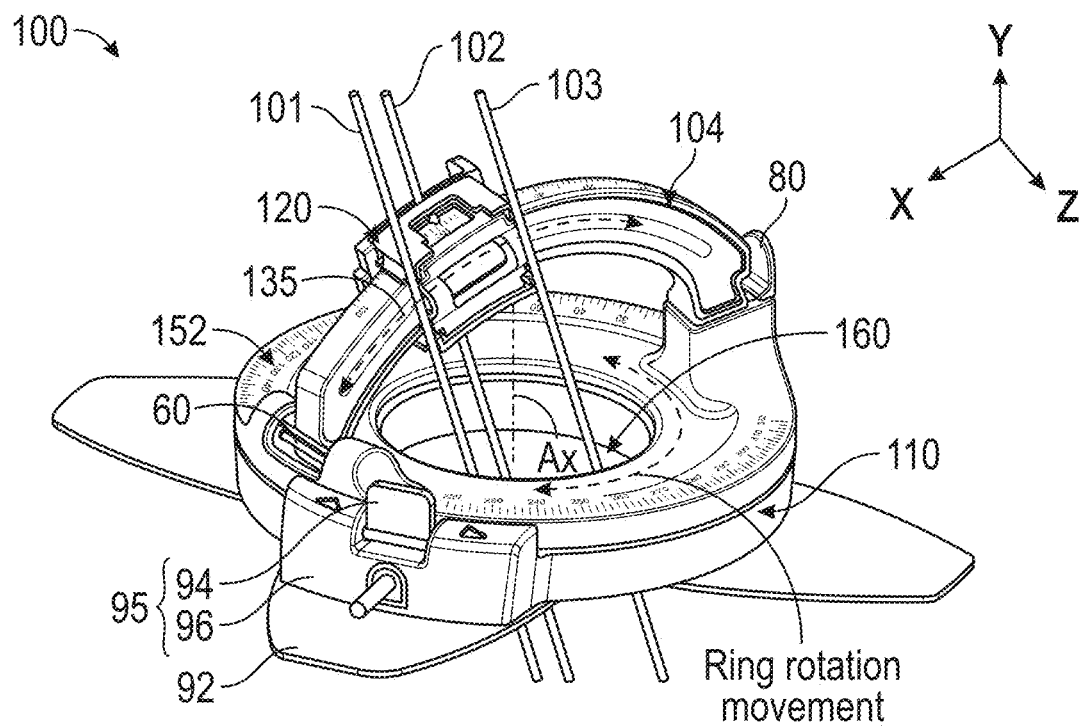
FIGS. 1A-1C are schematic diagrams showing an embodiment of a device and/or system for performing multiple ablation probe guidance in accordance with one or more aspects of the present disclosure.

In referring to the description, specific details are set forth in order to provide a thorough understanding of the examples disclosed. In other instances, well-known methods, procedures, components and materials have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description and/or illustration to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated. The term "position" or "positioning" should be understood as including both spatial position and angular orientation.

The term "about" or "approximately" or "substantially", when referring to a given value or values, as used herein means, for example, within 10%, within 5%, within 1%, or less. In some embodiments, the term "about" may mean within measurement or manufacture error. In this regard, where described or claimed, all numbers may be read as if prefaced by the word "about" or "approximately," even if the term does not expressly appear. The phrase "about" or "approximately" or "substantially" may be used when describing magnitude and/or position or orientation to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical range, if recited herein, is intended to include all sub-ranges subsumed therein.

As will be appreciated by those skilled in the art, some aspects of the disclosure may be embodied, at least in part, as a computer program product embodied in any tangible medium of expression having computer-usable program code stored therein. For example, some aspects described below with reference to flowchart illustrations and/or block diagrams of methods, apparatus (systems) and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram.

In the following description, reference is made to the accompanying drawings which are illustrations of exemplary embodiments. It is to be understood, however, that those skilled in the art may develop other structural and functional modifications without departing from the novelty and scope of the instant disclosure.

One or more devices, systems, methods and storage media for performing guidance for multiple ablation probes are disclosed herein. In one or more embodiments, the configurations, methods, apparatuses, systems and/or storage mediums may be combined to further enhance the effectiveness in guiding the probes. Several embodiments of the methods, which may be carried out by the one or more embodiments of an apparatus, system and computer-readable storage medium of the present disclosure are described in reference to the enclosed drawings.

<Multi-Probe Medical Guidance Apparatus>

Figure 1B:
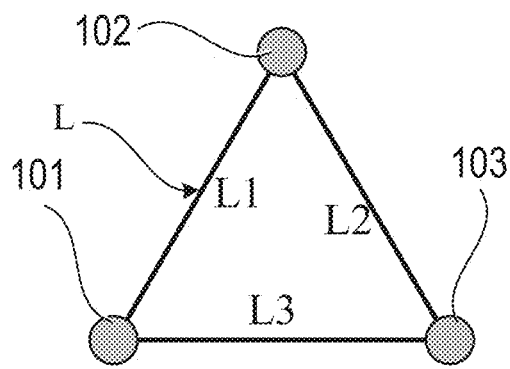
Figure 1C:
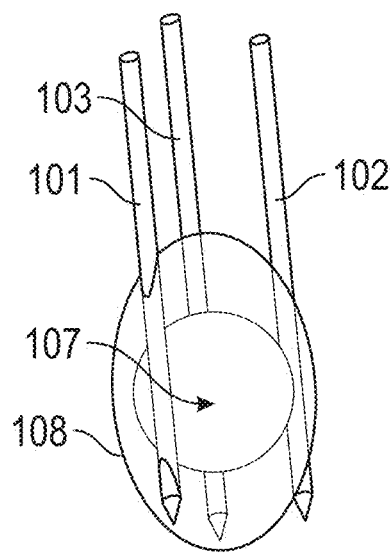

FIGS. 1A-1C show one embodiment of an apparatus for guiding multiple ablation probes, in accordance with at least one aspect of the present disclosure. FIGS. 1A, 1B, and 1C are schematic diagrams showing exemplary hardware and methods of using a medical guidance apparatus and/or system for performing multiple probe percutaneous interventions. FIG. 1A shows a perspective view of a medical guidance apparatus 100 configured for multi-probe guidance. The medical guidance apparatus 100 includes a rotatable portion 152 (a rotatable ring) which is arranged on a base assembly 110, an arc-shaped guide 104 (arc member) which is connected at two ends thereof with the rotatable portion 152, and a probe holder 120 which is mounted on the arc guide 104. A plurality of fiducial markers (not shown) may be included (embedded) in the base assembly no and/or the rotatable portion 152 for device-to-image registration. The base assembly no and the rotatable portion 152 align each other around an axis Ax of a cylindrical opening 160.

The medical guidance apparatus 100 operates in a three-dimensional (3D) space defined by a set of X, Y, Z axes. As used herein, the term "position" refers to the location of an object or a portion of an object in the three-dimensional space (e.g., three degrees of translational freedom along Cartesian X, Y, Z coordinates); the term "orientation" refers to the rotational placement of an object or a portion of an object (three degrees of rotational freedom—e.g., roll, pitch, and yaw); the term "posture" or "position" refers to the position of an object or a portion of an object in at least one degree of translational freedom and to the orientation of that object or portion of the object in at least one degree of rotational freedom (up to six total degrees of freedom); the term "shape" refers to a set of posture, positions, and/or orientations measured along a direction (axis) of the object. For example, as measured or seen along the Y axis, both the base assembly no and rotatable portion 152 have a ring shape, and are aligned to the opening 160 of a cylindrical shape. In addition, as measured or seen along the Y axis, the arc guide 104 has an arc shape. As used herein, the term arc or arc guide (or arc shaped guide) refers to any portion (other than the entire curve) of the circumference of a circle having a given diameter.

The base assembly no is configured to be mounted onto a subject or patient (not illustrated). In one embodiment, the medical guidance apparatus 100 is a needle guidance device configured to be placed on the surface (skin) of a patient's body so that a probe or needle-like instrument can be inserted through a needle entry point on the skin of the patient, via the opening 160. To that end, base assembly no and rotatable portion 152 of the medical guidance apparatus 100 may be first fixed to the patient with an adhesive patch 92 provided in the lower surface (bottom) of the base assembly 110. Thereafter, the probe or needle-like instrument is mounted on the arc guide 104 using the probe holder 120. Since the arc guide 104 is detachable from the rotatable portion 152, the probe or needle-like instrument can be mounted onto the guidance apparatus 100 after the base assembly 110 and rotatable portion 152 are mounted on the patient. Once mounted on the guidance apparatus 100, the needle-like instrument is automatically (or manually) guided to the target area of interest using navigation software, as described below. In some embodiments, the base assembly no may be attached to the patient's skin with straps or belts (as opposed to adhesive patch 92). Rotation of the rotatable portion 152 with respect to the base assembly no can be controlled electronically or manually. To monitor the rotational position of rotatable portion 152 with respect to base assembly no, reference tracking marks 174 are provided on the circumferential surface of the rotatable portion 152 and/or the base assembly no. To secure the rotatable portion 152 at a desired rotational position or orientation, a cam/lever (or break) mechanism 95 comprised of a cam 96 and lever 94 is provided as part of the base assembly no. In one embodiment, a rotary encoder (not shown) to measure a position of the rotatable portion 152 with respect to the base assembly no may be provided. In addition, a circuit board and a microcontroller (not shown) may be provided to process the signals from the rotary encoder. To facilitate rotation of the rotatable portion 152 with respect to the base assembly no, ball bearings and/or a motor may be provided. The rotary encoder, circuit board, and microcontroller may be provided within the body of base assembly no.

The rotatable portion 152 is a rotatable ring which rotates around its own axis. In FIG. 1A, the axis Ax is parallel to a first axis (Y) of the 3D space. The probe holder 120 is mounted on the arc guide 104 and is configured to slide along an arcuate path 135. Therefore, in the 3D space of FIG. 1A, the axis of the arc guide 104 is parallel to the second axis (Z). Accordingly, the probe holder 120 is rotatable around the second axis (Z) by being mounted to the arc guide 104 and slideable along the arcuate path 135. In turn, the arc guide 104 is removably attached to the rotatable portion 152 at two ends thereof, or the arc guide 104 can be formed integrally with the rotatable portion 152.

In embodiments where the arc guide 104 is removably attached to the rotatable portion 152, the arc guide 104 includes a locking mechanism 80 and a pivotable mechanism 60. In one example, the locking mechanism 80 is a snap joint (or clip type) mechanism, and the pivotable mechanism 60 is a C-clip at the end of the arc guide 104 connected to a pin provided on the rotatable portion 152. In that case, the arc guide 104 can be unlocked from the rotatable portion 152 by operating the snap joint locking mechanism 80, and then the arc guide 104 can be pivotably rotated to an open position. This gives access to the user for ease of observation, confirmation, and/or manual handling of needle insertion. In addition, if more room is necessary for accessing to the insertion area of interest, the pivotable mechanism 60 can be disengaged from the rotatable portion 152 (by disengaging the C-clip from the pin) so that the entire arc guide 104 and needle holder 120 can be removed from the rotatable portion 152.

The probe holder 120 is designed to accept a plurality of probes, needles, or needle-like instruments. In FIG. 1A the probe holder 120 can accept up to three probes: a first probe 101, a second probe 102, and a third probe 103. FIG. 1B depicts a top down view of the insertion points (at the patient's surface) of each probe 101, 102, and 103. The probe holder 120 is setup to orient the probes parallel to each other and spaced apart by a predefined distance L. The predefined distance L can be the same distance between all probes, such that the arrangement of the three probes can form an equilateral triangle, as shown in FIG. 1B. In other embodiments, the predefined distance L can be given by the design and arrangement of the various probe guiding channels formed in the probe holder 120, as described below with reference to FIG. 3A. The distance L can be different between adjacent probes. For example, a first distance L1 between probe 101 and probe 102 may be different from a second distance L2 between the probe 102 and probe 103; and, a third distance L3 between probe 103 and probe 101 can be different from the first and second distances L1 L2.

FIG. 1C depicts an exemplary arrangement of the ablation probes 101, 102, and 103 guided by the medical guidance apparatus 100 and placed around a tumor 107. With this arrangement, an ablation zone 108 is achieved with a summative effect of the three parallel ablation probes arranged at a same depth with respect to the entry surface points. Although three probes are depicted in this embodiment, it is not required that all three probes be inserted to obtain the summative effect. For example, in an instance where two parallel probes may achieve the desired summative effect to cover the ablation zone 108, then only two of the probes may be used. In other instances, more than three probes, or multiple probes arranged in a form other than parallel may be necessary to achieve the desired summative effect to cover the ablation zone 108. It is contemplated that, based on the novel techniques disclosed herein, a person of ordinary skill in the art will be able to derive various probe arrangements parallel or otherwise to obtain a desired summative effect.

FIGS. 2A-2C show another embodiment of a medical guidance apparatus 100 for guiding multiple ablation probes, in accordance with a further aspect of the present disclosure. FIG. 2A shows a perspective view of the hardware structure of the medical guidance apparatus 100 configured to guide a plurality of probes (201, 202, 203, and 204) in a conical manner. In FIG. 2A, the apparatus 100 includes a rotatable portion 152 which is rotatable around its own axis Ax with respect to the base assembly no. The probe holder 120 is mounted on the arc guide 104 similar to the embodiment of FIG. 1A. The probe holder 120 is rotatable around the second axis (Z) by being attached to the arc guide 104, as explained above in reference to FIG. 1A. The arc guide 104 is attached to, or integrally formed with, the first rotatable portion 152.

FIG. 2B shows a top down view of the insertion points (at the patient's surface) of each of the first probe 201, second probe 202, third probe 203, and fourth probe 204. As shown in FIG. 2B, at the patient's surface (skin), the probes are arranged to form a circle 207 (an insertion circle) which is centered at a center point 205. The center point 205 is a point along the axis Ax of the opening 160; the center point 205 is located at the plane (XZ plane) of a surface of the base assembly no which closest to the patient's skin. In other words, the center point 205 is at the intersection of axis Ax and the plane of the bottom surface of base assembly 110. Here, the center point 205 functions as a remote center of motion for the probe holder 120, but a guidance channel for each probe is intentionally offset from the center point 205 by a distance R. By offsetting the probe guidance channel a fixed distance R from the center point 205, the multiple probes 201, 202, 203, and 204 can be inserted (sequentially or simultaneously) in a conical pattern without colliding at the center point 205 of the device. As the rotatable portion 152 is rotated and each probe is inserted at a given angle with respect to axis Ax, a circle 207 of possible insertion points is made by the location of each guidance channel. The size of this circle 207 of possible insertion points is defined by the offset distance R of the probe guidance channel from the center point 205. In one or more embodiments, the offset distance R of the probe guide channel with respect to the center point 205 is fixed by the design of the probe holder 120 to ensure that a maximum number of probes of a certain diameter can be inserted without collision. The optimal offset distance for each guidance channel (i.e., the radius of the circle formed by the guidance channels) is defined as R is given by equation [1], as follows:

$$R=((D*N)+S)/2\pi, \quad [1]$$

where D is the diameter of the probe (or an average diameter of the plurality of probes), N is the maximum number of probes that will be used in a procedure, and S is a safety margin (minimum distance) to ensure there is no probe collision. Although this embodiment depicts only four probes, it is the safety margin S and the offset distance R for each guidance channel (for each probe) that defines the maximum number N of probes that the apparatus 100 can support. Without a safety margin S, the minimum radius of the circle 207 can be derived based on the diameter (size) of the probes, such that all probes abutt right up against each other. However, the safety margin S is provided to allow for spacing between insertion points to ensure prevention of probe collision. Therefore, the safety margin S can be set by the user or recommended by the device manufacturer.

The offset distance R and the number N of probes also depend on the size of the tumor and desired ablation zone. To have an optimal summative effect for ablation zone 108, the distance between the tips of the probes is also important. For example, a two centimeters probe tip to probe tip distance would work to ensure the formation of a synergistic ice ball having a radius of at least two centimeters (assuming an overlap of one centimeter). More than two centimeters distance between the tips of the probes could increase the probability of forming a non-synergistic ice ball such that the ablation procedure would not be successful. In other embodiments, other maximum distances could be manually set by the clinician, e.g., from a look-up table, from a combination of probe or energy source parameters, etc. Also, a maximum distance between probe tips could be defined manually by referring to the size of the tumor so that the user can avoid unreasonable tip positioning with the given size of the tumor. Moreover, a minimal distance between probe tips would be useful to avoid possible collision of the probes with each other.

In one or more embodiments, in particular in conical arrangement of plural probes, the device design will create a cylinder of unreachable area 208 below the center of insertion circle 207. That is, because the probes are inserted around various points on the insertion circle 207, there can be a small unreachable area 208 immediately below the skin of the patient in the middle of insertion circle 207. The diameter of this cylinder of unreachable area 208 is defined by the size of the insertion circle 207 formed by the arrangement of the multiple probes at the entry points. The diameter of the cylinder of unreachable area 208 is very small compared to the size of the tumor 107 or the size of the ablation zone 108. Indeed, if the ablation zone 108 is designed to ensure the formation of a synergistic ice ball assuming an overlap of energy at the probe tips, the cylinder of unreachable area 208 will be negligible in terms of probe guidance accuracy and ablation zone effectiveness. In a case where a single insertion is needed, or only as single probe or needle is to be inserted using the medical guidance apparatus 100 shown in FIG. 2A, the probe does not need to be offset from the center point 205. Indeed, it would be preferable to insert such single probe through the remote center of motion (through center point 205), so that the probe could be inserted from any angle without creating any unreachable area.

The embodiments of FIGS. 1A-1C and 2A-2C describe two notable features of the multi-probe medical guidance apparatus 100 disclosed herein. FIGS. 1A-1C show a medical guidance apparatus 100 capable of guiding up to three parallel probes (either simultaneously or sequentially) which is particularly desired in microwave ablation and irreversible electroporation. FIGS. 2A-2C show a medical guidance apparatus 100 capable of guiding multiple ablation probes in a conical configuration to bracket a tumor 107 into an ablation zone 108. This configuration is particularly desired for cryo-ablation processes. Although both embodiments are described separately, they are not mutually exclusive. The same medical guidance apparatus 100 shown in FIGS. 1A and 2A is capable of guiding multiple needles in either configuration (parallel or conical). The only difference is the arrangement of the probe guidance channels formed in the probe holder 120. Moreover, custom probe configurations are also possible by using conical trajectories combined with parallel trajectories; that is, it is possible to provide multi-probe insertion in a combination of both parallel pattern and the conical pattern. This combination may be beneficial in complex cases with irregularly shaped tumors or tumors close to sensitive structures such as the bowel or the like, and, therefore, various modifications may be made within the scope of the present disclosure.

FIG. 3A shows a top down view of a probe holder 120, according to another aspect of the present disclosure. The probe holder 120 includes a main body 122 and a plurality of doors 610a and 610b. FIG. 3A shows the probe holder 120 configured to simultaneously (or sequentially) hold and guide a plurality of probes in parallel. These probes can be of different sizes and diameters; for example, ablation probes in a gauge range of 18 to 13 can be used in the probe holder 120 shown in FIG. 3A. The probe holder main body (122) is mountable to the arc guide 104 and is secured to the arc guide 104 with a cam lock mechanism which has a locking lever 604. In FIG. 3A, the probe holder 120 includes a first door 610a and a second door 610b respectively affixed to side surfaces of the probe holder 120 by a first set screw 626a and second set screw 626b. The probe holder 120 is mounted onto the arc guide 104 and is configured to move along an arcuate path 135 defined by the shape of arc guide 104. The locking lever 604 locks or secures the probe holder 120 at a desired angle along the arc guide 104. The arc guide 104 may include angular reference marks 174 along at least part of one or more surfaces thereof. For example, in FIG. 3A, the angular reference marks 174 are provided on the top surface of arc guide 104.

A plurality of grooves, which serve as channels (guide channels) for the multiple probes, are formed on surfaces of the probe holder 120 and the doors 610a and 610b. In FIG. 3A, the first door 610a includes two grooves which match the two grooves formed on a first surface of the probe holder 120. In this manner, the combination of the first door 610a and a first surface of the probe holder 120 forms two guide channels 207a and 207b for securing therein corresponding first and second probes (not shown). The second door 610b includes one groove which matches a third groove formed on a second surface of the probe holder 120. The combination of the second door 610b and the second surface of probe holder 120 form a third guide channel 207c for securing therein a third probe (not shown). The doors 610a and 610b can be tightened and loosened separately by using a designated set screw. Each door and set screw pair is designed in such a way that even when loosened to its maximum adjustment level, the door still stays attached to the probe holder 120. The adjustability of the doors by the designated set screws allows the user to securely fix in place the probes of different size, or to have each probe with a certain degree of slack (loosen) to safely slide freely along the guide channel while being guided to any depth based on the user preference.

To better control the depth of probe insertion, the top surface (or outer most surface) of the probe holder 120 is made flat such that the top surface of the probe holder 120 is perpendicular to each guide channel 207a, 207b, and 207c. In this manner, if three (3) probes are inserted, the three probes will be parallel to each other, and all probes could be inserted the same depth so as to have the tips of the probes at the same distance along the insertion trajectory which is a desired configuration for multi-probe ablations. FIG. 3B shows an example where the top surface 121 of the probe holder 120 is perpendicular to the guide channels of probes 101 and 102. In addition, the top surface 121 is substantially tangential (tangent) to the circumference 155 which corresponds to the curvature of the arc guide 104. In this manner, when the probe holder 120 slides along the arcuate path 135, the probes 101 and 102 will be inserted the same depth (H) from the top surface 121 regardless of the position (angle) where the probe holder 120 is rotated to.

FIGS. 3C and 3D both show a top down view of a guide channel 207a configured to receive therein needle-like instruments of a plurality of sizes. The guide channel 207a is formed by the combination of two v-shaped grooves; a first "V" groove is provided in a surface of the probe holder 120 and a second "V" groove is provided in the inner surface of the door 610a. Specifically, FIG. 3C shows a top down view of the first guide channel 207a receiving therein the first probe 101. In this case, the probe 101 has a first diameter D1. FIG. 3D shows a top down view of the first guide channel 207a receiving therein the first probe 101. In this case, the probe 101 has a second diameter D2 larger than diameter D1. As the spacing between the door and the probe holder increases, so does the maximum diameter of a probe which can be inserted through the grooves.

As shown in FIGS. 3C and 3D, the profile of the groove allows it to form a channel guide 207a which can adequately accommodate multiple gauges of needles or probes. Since each half groove is a triangle, the contact points (between the probe and the groove) are equally distributed around the circumference of the probe (up to a certain gauge size, limited by the dimension of the groove). This depends on the angle $\beta$ of the groove, for example for $\beta=90$ degrees, the contact between the probe and the groove is equally distributed. Regardless, the 'angle of contact' will be the same for all gauges. The v-shaped groove is considered advantageous in that it can adequately accommodate multiple gauges of needles or probes (up to a certain gauge size) and it can provide uniform probe holding force because the contact between the probe and the groove is equally distributed around the circumference of the probe. Having the contact between the probe and the groove equally distributed around the circumference of the probe can provide improved accuracy in probe guidance and it can prevent damage (e.g., bending or collapsing) of the probe. It is contemplated that persons of ordinary skill in the art may modify the groove angle $\beta$ to accommodate various gauges and types of probes. In addition it is contemplated that each guide channel could be modified to any other cross-sectional shape to receive needle-like instruments (e.g., catheters, endoscopes, or optical probes). However, if the profile of the guide channel was a semi-circle on each half of the groove, the distance between contact points would be a fixed regardless of the needle gauge (except for the one size which will be fully encompassed by the circular groove). Here, the probe channels on the probe holder 120 may be labeled (such as numbering the channels or showing the range of sizes permitted in channel) so that a user can be instructed what channel to use to insert a given probe.

For conical probe arrangement, the probe holder 120 can be modified such that only one guide channel is provided, and the arc guide 104 and probe holder 120 are rotated by the rotational action of the rotatable portion 152 around its own axis Ax. In this case, the multiple probes can be inserted sequentially using the guidance apparatus 100. Alternatively, the probe holder 120 may include more than one guide channel, e.g., at least two guide channels 207a and 207b formed at a predetermined angle with respect to the axis Ax, and the probe holder 120 and arc guide 104 may be rotated by the action of the rotatable portion 152.

<Multi-Probe Planning and Guidance>

Figure 4:
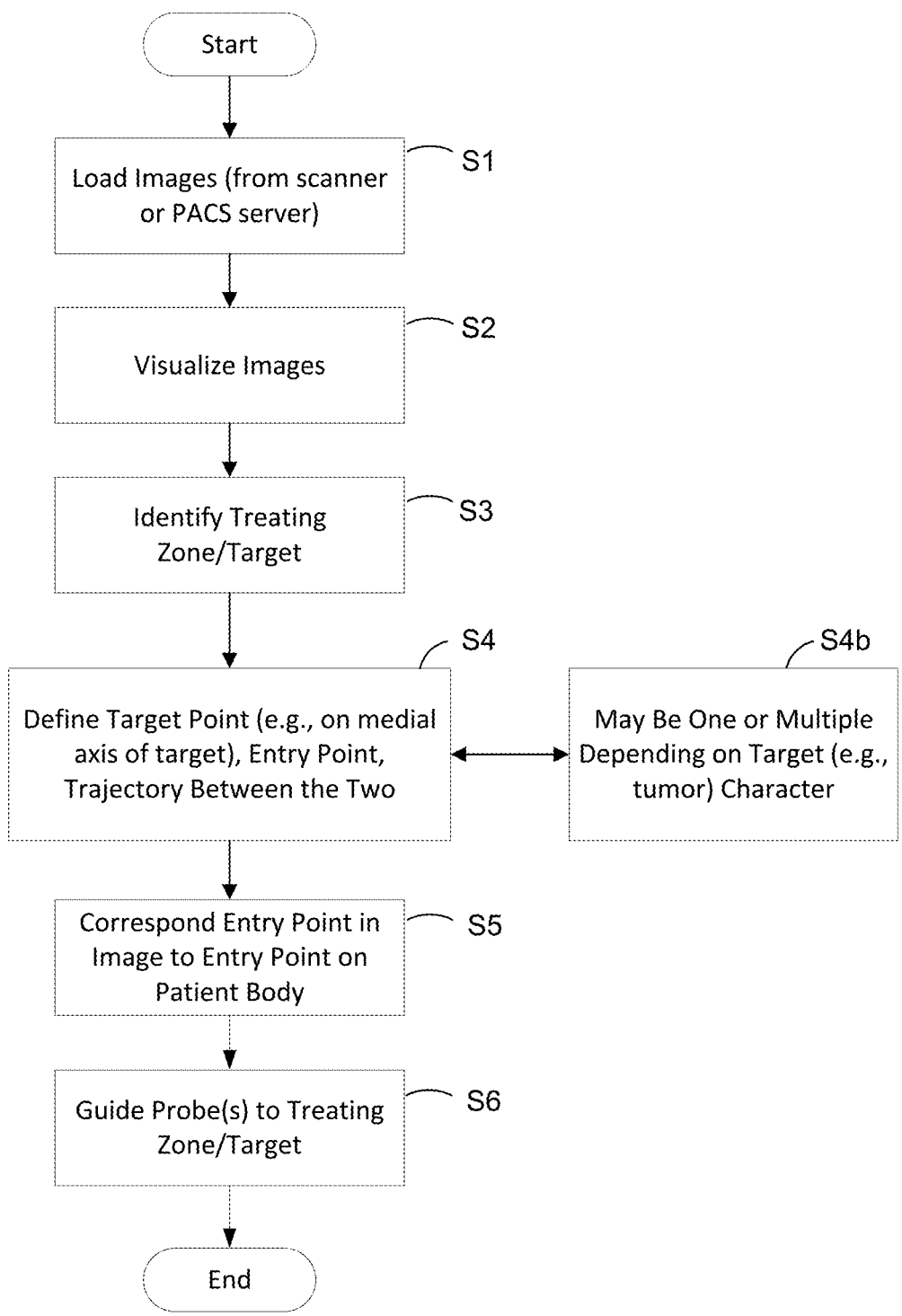
FIG. 4 is a flow chart showing at least one embodiment of a method for performing ablation planning and/or ablation in accordance with one or more aspects of the present disclosure.
Figure 5:
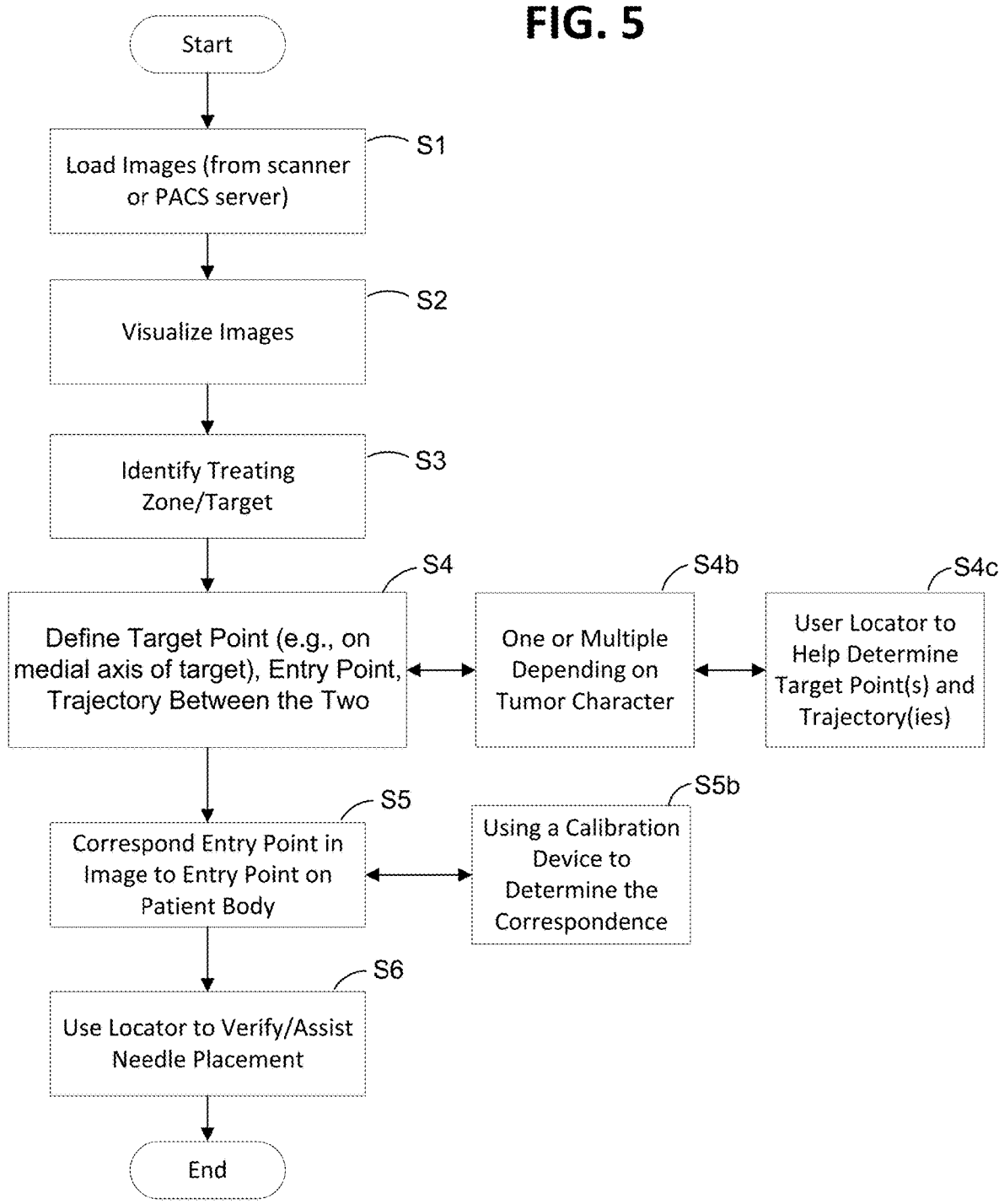
FIG. 5 is a flow chart showing at least another embodiment of a method for performing ablation planning and/or ablation in accordance with one or more aspects of the present disclosure.
Figure 6A:
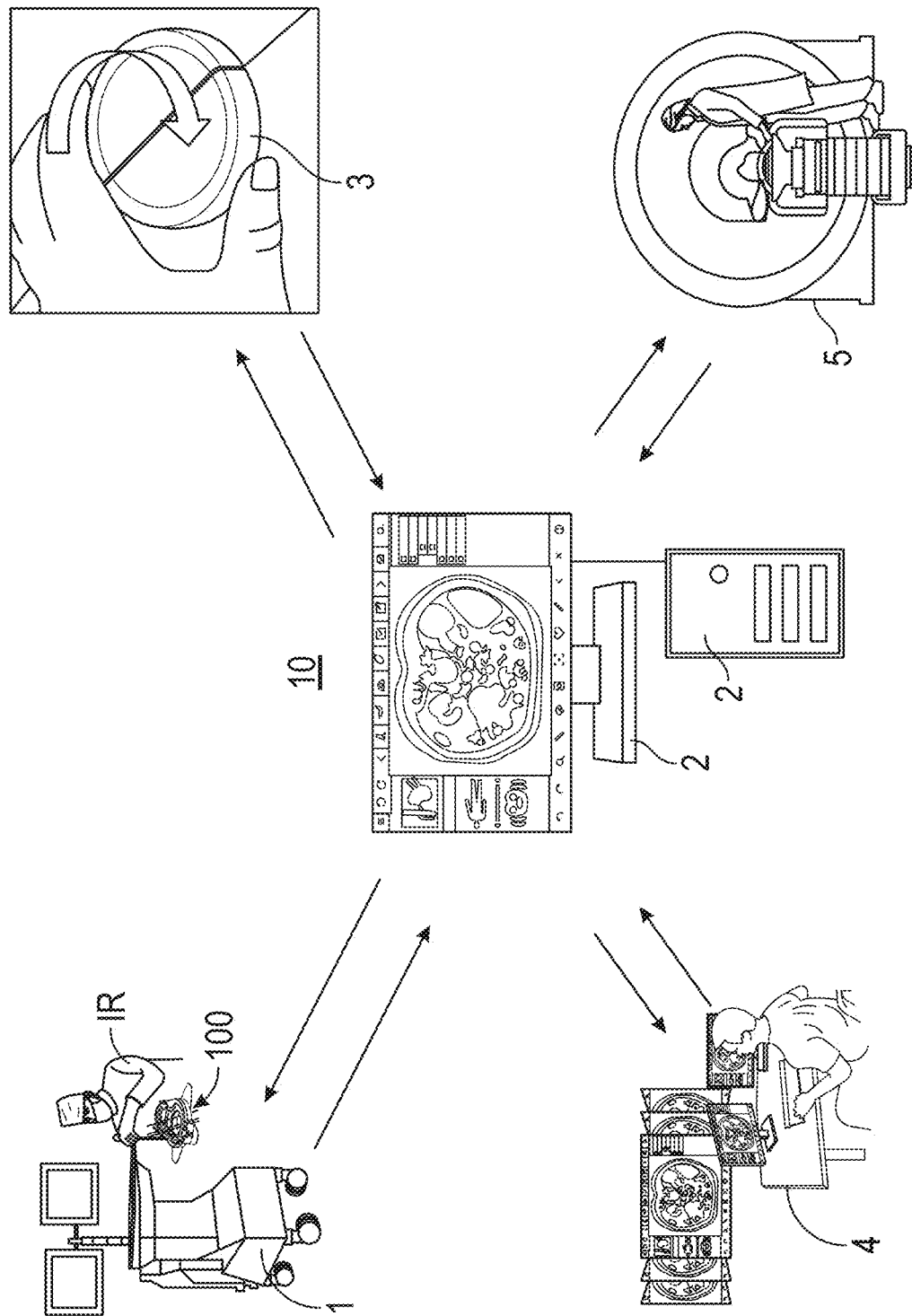
FIG. 6A is a schematic diagram showing an embodiment of a system for performing ablation planning and/or ablation in accordance with one or more aspects of the present disclosure.

In accordance with at least one aspect of the present disclosure, one or more methods for performing ablation planning and/or ablation performance, and one or more methods for guiding multiple probes are provided herein. At least FIGS. 4-5 illustrate flowcharts of at least one respective embodiment of a method for performing ablation planning and/or ablation performance using an ablation device, a system (e.g., a system 10 as shown in FIG. 6A), or storage medium storing instructions. As shown in FIG. 6A, a system 10 may include an ablation device 1, a computer 2 (which may include software and/or hardware for implementing the ablation planning and/or performance), a locator device 3 (such as, but not limited to, an image-plane localizer), a Picture Archiving and Communication System (PACS) server 4, and an image scanner 5 (such as, but not limited to, a CT scanner, MRI device or other scanning apparatus). In the environment of FIG. 6A, and intervention radiologist (IR) uses the medical guidance apparatus 100 to perform multi-probe percutaneous interventions with the ablation device 1.

As shown diagrammatically in FIG. 6A, the ablation planning methods of the present disclosure may be involved with all major aspects of navigation planning, probe guidance, and ablation performance. For example, in the system 10, the computer 2 may communicate with the image scanner 5 to request information for use in the ablation planning and/or performance, such as, but not limited to, bed or slice positions, and the image scanner 5 may send the requested information along with the images to the computer 2 once a clinician uses the image scanner 5 to obtain the information via scans of the patient. The computer 2 may also communicate and be used with a locator device 3 (such as an image-plane localizer that may be a patient-mount device and may be rotated as shown to help locate to biological object, such as a lesion or tumor) to obtain information from the patient when conducting ablation planning and/or ablation performance. The computer 2 may further communicate with the PACS server 4 to send and receive images of a patient to facilitate and aid in the ablation planning and/or performance. Once a plan is established, a clinician may use the computer 2 along with ablation device 1 to consult an ablation chart or plan to understand the shape and/or size of the targeted biological object to be ablated. Each of the ablation device 1, the computer 2, the locator device 3, the PACS server 4 and the scanning device 5 may communicate in any way known to those skilled in the art, including, but not limited to, directly (via a wired or wireless communication network) or indirectly (via one or more interconnections of computer 2 with one or more of the ablation device 1, the locator device 3, the PACS server 4 and the scanner 5) in response to user interaction.

One or more embodiments of the ablation planning and performance apparatuses and systems, and methods and storage mediums may operate to improve the determination of the needle or probe trajectory. One or more embodiments of the present disclosure operate to reduce the number of scans, and consequently reduce the insertion and trajectory determination time. One or more embodiments greatly assist clinicians, including during the stages of determining insertion point, determining trajectory, performing initial probe insertion and performing full probe insertion, by providing a probe tracking and guidance system for faster execution of the ablation plan and better accuracy in positioning a probe. The tracking and guidance system not only tracks the probe position and orientation, but also provides cues for visualization software with the patient's lesion and critical structures from an IR's or other clinician's point of view. This visualization may be updated in real time to account for motion due to respiration and tissue deformation. The tracking and guidance system can also give IR the ability to define the trajectory and insert the probe remotely through a robotic device placed on the body of the patient or situated near the patient, controlling the probe from outside of the imaging (CT for example) suite. The remotely controlled operating system may shorten procedures by reducing the time moving in and out of the CT suite and mitigating the exposure to radiation.

Preferably, the method(s) may include one or more of the aforementioned ablation planning and performance steps, including, but not limited to, one or more of the following: (i) loading images (e.g., from a scanner, a PACS server, or other scanning device/system, or using a fresh or newly scanned image) (see step S1 in FIG. 4); (ii) visualizing images (e.g., such as by showing multiple panes (views, such as, but not limited to, axial, coronal, sagittal, 3 dimensional (3D), etc.) (e.g., each view may represent a different aspect of an image (e.g., a CT DICOM image); showing at least one pane of an image; loading an image (e.g., a CT DICOM image) and displaying it on a computer for visualization purposes; allowing a user to interact with a displayed image in one or more panes by moving at least one line (e.g., an axis or axes) to cut through one or more planes to reformat a 3D data set and display the reformatted slices in the 3D view; etc.)) (see step S2 in FIG. 4); (iii) identifying a treating zone or target (e.g., a lesion or tumor) (see step S3 in FIG. 4); (iv) defining a target point, an entry point and a trajectory between the target and entry points (see step S4 in FIG. 4) (as shown in step S4*b*, Step S4 may include repeating the process if there is one trajectory or there are multiple trajectories (and multiple target points) depending on a characteristic of a tumor or lesion); and (v) correspond the entry point in a particular image to an entry point for a body of the patient (see step S5 in FIG. 4). Determination of the target points (and the number of target points) may be at the discretion of the clinicians in one or more embodiments, or may be dependent upon the characteristic(s) of the target biological object, such as a lesion or tumor (e.g., a size of the lesion or tumor, a shape of the lesion or tumor, etc.). In one or more embodiments of the present disclosure, a method is provided to determine or suggest a target point or points that is clinically the best choice (e.g., mathematically, statistically, etc.) for placement of the target point(s). In one or more embodiments, target point(s) may be determined by finding or determining a medial axis or center line of the target or treating zone (see step S4 of FIG. 4). The concept of "medial axis" is described, for example, by Fritsch et al., "The Multiscale Medial Axis and its Applications in Image Registration," Pattern Recognition Letters, vol. 15, pp. 445-452 (May 1994), and it refers to a set of points equidistant from tangent points on opposite surfaces of a region of interest (e.g., tumor) and located at the intersections of orthogonal lines from the tangent points within the surfaces.

For any identification of a target or targets step(s) discussed herein (such as, but not limited to, step S3 of FIGS. 4-5; step(s) S4, S4*b* of FIG. 4; step(s) S4, S4*b*, S4*c* of FIG. 5; etc.), any method of identifying a target biological object or zone, including those known to those skilled in the art, such as a clinician, and including the additional method(s) provided herein, may be employed. For example, in one or more embodiments, a target zone and target points are to be identified. A target zone may be identified by an image segmentation method(s). To that end, clinicians may initially define a few points, called seeds, which may or may not be the target points within an identified a target region, such as a lesion or tumor region. In one or more embodiments, an active contour model, such as a snake algorithm (see e.g., one example explained by C. Xu and J. L. Prince in "Gradient Vector Flow: A New External Force for Snakes", Proc. IEEE Conf. on Comp. Vis. Patt. Recog. (CVPR), Los Alamitos: Comp. Soc. Press, pp. 66-71, June 1997), may be used to iteratively determine a boundary of the target region.

The initial seeds may not converge to a true boundary quickly, so, in one or more embodiments, a watershed method (see e.g., one example explained by Gouze A., De Roover C., Herbulot A., Debreuve E., Barlaud M., Macq B. in "Watershed-driven Active Contours for Moving Object Segmentation", in Proceedings of IEEE International Conference on Image Processing (ICIP), vol. II, pp 818-821, Genova, Italie, September 2005) may be used together with the snake algorithm to make the segmentation smoother and faster. Compared to manually drawing a boundary of a target region, such as a lesion or tumor region, such a method or methods generate a far more accurate and consistent boundary, which may be used to determine a volume of a target (e.g., a tumor or lesion) and may be used in a later stage for quantitatively characterizing the tumor or lesion and assessing ablation results. The resulting boundary forms a target zone.

Additionally or alternatively, one or more method(s) of the present disclosure may further include performing ablation planning and/or performance with a locator device 3 as shown in FIG. 6A. In addition to the steps shown in FIG. 4 (the details of which are aforementioned and will not be repeated further), such one or more method(s) employing a locator device, such as the locator device 3 may further include, but are not limited to, one or more of the following: (i) using a locator, such as the locator device 3, to help determine the target point(s) and trajectory(ies) in steps S4 and/or S4b (see also steps S4, S4b and S4c in FIG. 5); (ii) using a calibration device (e.g., such as, but not limited to, fiducial markers, systems and methods of registration, such as those disclosed by this applicant in U.S. patent application Ser. No. 14/755,654 and published in U.S. Pat. Pub. No. 2017/0000581, which are incorporated by reference herein in their entireties) to determine or assist with the correspondence step of S5 (see also steps S5 and S5b in FIG. 5); and (iii) using a locator, such as the locator device 3, to verify and/or assist with needle placement when performing ablation for the patient (see step S6 in FIG. 5). In one or more embodiments of the present disclosure, at least one embodiment of a method for performing ablation planning or ablation performance is to use such calibration device(s) and/or locator device(s) to increase or maximize the success of the ablation procedure depending on one or more variables, such as, but not limited to, needs of the patient, characteristics of the lesion/tumor, if movement of the patient is needed during the procedure, etc. In one or more embodiments of the present disclosure, such calibration device(s) and/or locator device(s) assist a clinician in finding a medial axis or center line of the target biological object, such as a lesion or tumor.

In one or more embodiments, workflow for a particular procedure, such as ablation planning and/or ablation performance, may be combined with segmentation, registration and differential image view steps to provide better differential images (such as, but not limited to, segmentation, registration and differential image steps disclosed in PCT/US2018/020752, published as WO/2018/175094, which is incorporated by reference herein in its entirety), which avoid the generation of misleading artifacts in images and/or avoid other issues with procedure-related problems. Differential images are a quick way to give clinicians feedback of ablation results. While thermal maps may be used in one or more embodiments, such thermal maps may be affected by environmental changes, such as blood flow, and measurements may not be easily localized depending on the circumstances. Various types of ablation may be used in one or more embodiments (e.g., cryoablation, microwave ablation, laser ablation, etc.). While cryoablation may be used, iceballs may form, and are very visible under MRI. Ultrasound may be used in one or more of the methods discussed herein for navigation, and some indication of an ablation result may be obtained from the same tool. However, ultrasound images may be noisy and may be hard to quantitatively measure. Regardless of which detection or monitoring tool/technique is employed, the integration of the workflow with segmentation, registration and differential image view steps reduces and/or avoids such issues to provide a useful differential image or images for clinicians to use in one or more procedures (e.g., ablation, radiotherapy, etc.).

For ablation procedures, one probe ablation or multi-probe ablation may be performed. For multi-probe ablation, serial or parallel multi-probe ablation may be performed. In serial ablation, ablation is done in sequence of one probe being inserted, ablated, confirmed, then another probe being inserted, ablated, confirmed, and repeating such steps if more probes are needed. In parallel ablation, all probes are inserted before ablation starts. Clinicians may decide which ablation approach is chosen. No matter which approach is chosen, a confirmation stage is needed after the ablation is done. Based on information from each confirmation, a clinician may determine whether additional ablation is needed, and, if so, where to plan for the next probe to be used. Confirmation provides clinicians with an indication as to whether the margin is reached or overreached to evaluate the results of the ablation procedure.

To aid clinicians in performing confirmation steps, one or more embodiments of the present disclosure may include confirmation with margin view so that confirmation or any other determination process requiring clear image feedback may be performed more effectively (such as, but not limited to, confirmation steps disclosed in PCT/US2018/020752, which is incorporated by reference herein in its entirety). While quantitative measure of coverage is useful, a visual quick assessment is also very useful in one or more applications. The margin view gives a better view than the common overlay of before and after ablation images to more easily and effectively determine the success of the ablation process. In one or more embodiments, the target(s), such as lesion(s) or tumor(s) may be segmented before and after ablation occurs, and differentiation between the two sets of segmented target images may be determined. Thereafter, the differential may be overlaid on the after-ablation images to evaluate the ablation process. Additionally or alternatively, one or more method(s) of the present disclosure may further include performing ablation planning and/or performance with a locator device as shown in FIG. 4 and in FIG. 5. One or more embodiments of methods for evaluating or determining a margin view may include, but are not limited to, one or more of the following: (i) loading images (e.g., from a scanner, a PACS or other scanning device/system, or using a fresh or newly scanned image) (see step S1 in FIGS. 4-5); (ii) visualizing images (e.g., such as by showing multiple panes (views) (e.g., each view may represent a different aspect of the image); as described above for step S2 in FIGS. 4-5; (e.g., in medical image software, such as, for example, the application shown in PCT/US2018/020752, which is incorporated by reference herein in its entirety); as otherwise described herein; etc.) (see step S2 in FIGS. 4-5); (iii) performing device registration (also referred to herein as device calibration) to make a correct correspondence or alignment between an image and real world dimensions for a patient (see e.g., steps S5 and/or S5b of FIG. 4 and/or FIG. 5 which may be incorporated into or used as a configuration or registration step; see also, device registration as discussed in PCT/US2018/020752, which is incorporated by reference herein in its entirety); (iv) identify a target or target(s), such as a zone or biological object (see step S3 of FIGS. 4-5); (v) segmenting the identified targets (at one reference point in the planning or procedure (e.g., before moving a needle, before performing ablation, before performing the next iterative or incremental planning step (either during the procedure or in simulation or planning), before moving a patient, etc.)—also referred to herein as "targets (1)", i.e., the targets identified at stage (1)); (vi) performing an incremental planning or performance step (e.g., move a needle, insert a new probe or needle, perform ablation, perform the next planning step, moving a patient, etc.); (vii) re-scanning the targets or obtaining newly scanned images of the targets after performing the incremental planning or performance step; (viii) visualizing images (e.g., such as by showing multiple panes (views) (e.g., each view may represent a different aspect of the image); as described above for step S2 in FIGS. 4-5; as otherwise described herein; etc.)); (ix) identifying a target or target(s), such as a zone or biological object (which may be the same or similar to step S3 of FIGS. 4-5 such that the above details regarding same are not repeated herein); (x) segmenting the re-scanned targets (at a second reference point in the planning or procedure (e.g., after moving a needle, after moving or adding a probe, after performing ablation, after performing the next iterative or incremental planning step (either during the procedure or in simulation or planning), etc.)—also referred to herein as "targets (2)", i.e., the targets as re-scanned at stage (2) after stage (1)); (xi) performing image registration (e.g., before conducting differentiation of current images and previous images); (xii) performing differentiation of current images (e.g., images of stage (2)) and previous images (e.g., images of stage (1)) to enhance the view of the effect of the procedure (e.g., ablation (especially when using microwave or radiofrequency (RF) ablation (in one or more embodiments, differentiation subtraction may not be needed for cryoablation)), radiotherapy, etc.); and (xiii) overlaying the differential on the current images (e.g., images of stage (2)). Image segmentation and registration may be performed using any method known to those skilled in the art, such as a clinician.

The image differentiation may be used to enhance the visualization of an ablation result, monitor probe progression during insertion, or to track any other incremental step in a procedure (e.g., ablation, radiotherapy, etc.). By way of example, a concept of such an enhancement after performing ablation is shown in PCT/US2018/020752, which is incorporated by reference herein in its entirety. The target or target zone of a biological object (such as a lesion or tumor) is surrounded by an ablation zone or ablated zone (once ablation is performed). As such, in one or more embodiments, such as when performing differentiation and overlaying the differential on the current image(s) of stage (2) or final images, a margin map is formed. The margin map may be used by a clinician to determine whether or not to edit a procedure plan and/or to evaluate whether the plan or procedure is optimal (e.g., the best option available) or has been successful (and to gauge how successful). This improved ability to measure success is good for feedback (such as for the clinician, patient, hospital, other clinicians consulting such results, etc.), and provides an outcome oriented application in one or more embodiments of the present disclosure. For example the percent of the margin (and/or other metrics of the margin) may be used to indicate how well the procedure went. A minimum or a maximum of the margin view or map may be set or predetermined by a clinician. The treatment or target zone may be displayed, overlaid on the target zone or target object (segmented), e.g., a tumor or lesion.

Additionally or alternatively, clinicians may perform simulations with one or more embodiments of the planning methods/software of the present disclosure to create an optical plan, to accommodate one or more variables (e.g., patient movement during the procedure, tissue deformations, etc.), and to evaluate the potential outcome. By way of at least one example, a simulation of an ablation zone (e.g., an ice ball for cryoablation, a balloon for microwave ablation, etc.) may be conducted. By way of another example, a simulation may be performed to mimic tissue deformation. For example, if clinicians segmented an organ or tumor (suppose an oval shape for purposes of the example simulation), the medial axis algorithm may take the segmented object as input and generate a medial axis output (typically it is a curve), which may be overlaid on the segmented object. By dragging and manipulating the medial axis curve, the curve may change its shape and location in space. Due to the fact that a volume may be reconstructed from a medial axis curve, the deformation may be simulated or obtained by dragging and manipulating the medial axis.

One or more embodiments of the ablation planning and performance apparatuses and systems, and methods and storage mediums of the present disclosure may operate to reduce the number of iterations for the determination of the insertion point(s) and trajectory of the probe after being inserted into the entry point(s). This is beneficial for reducing exposure to radiation when dealing with CT scans and reduces the total time of scanning when dealing with any type of scan, including, but not limited to, CT, MRI or otherwise. In one or more embodiments, registration with fiducial markers (such as a sticker grid) may be used on the patient at or near an insertion point before conducting a CT/MRI scan. This registration step helps to accurately correlate physical dimensions to what to see in the scanned images.

After a target zone is identified, clinicians may pick up a point or a few points within the target zone as target point(s). From there on, an ablation zone (for example iceball) may be defined on or around the target zone (e.g., in the case of the iceball example, the ball may be centered on the ablation zone). While clinicians may pick target points by trial and error, such trial and error leads to inefficiencies, such as, but not limited to, longer procedure time, more invasive and repeated steps (e.g., needle or probe insertion/movement), lack of accuracy, etc.

Figure 6B:
FIGS. 6B-6C are diagrams showing at least one embodiment of multi-probe ablation in accordance with one or more aspects of the present disclosure.
Figure 6C:
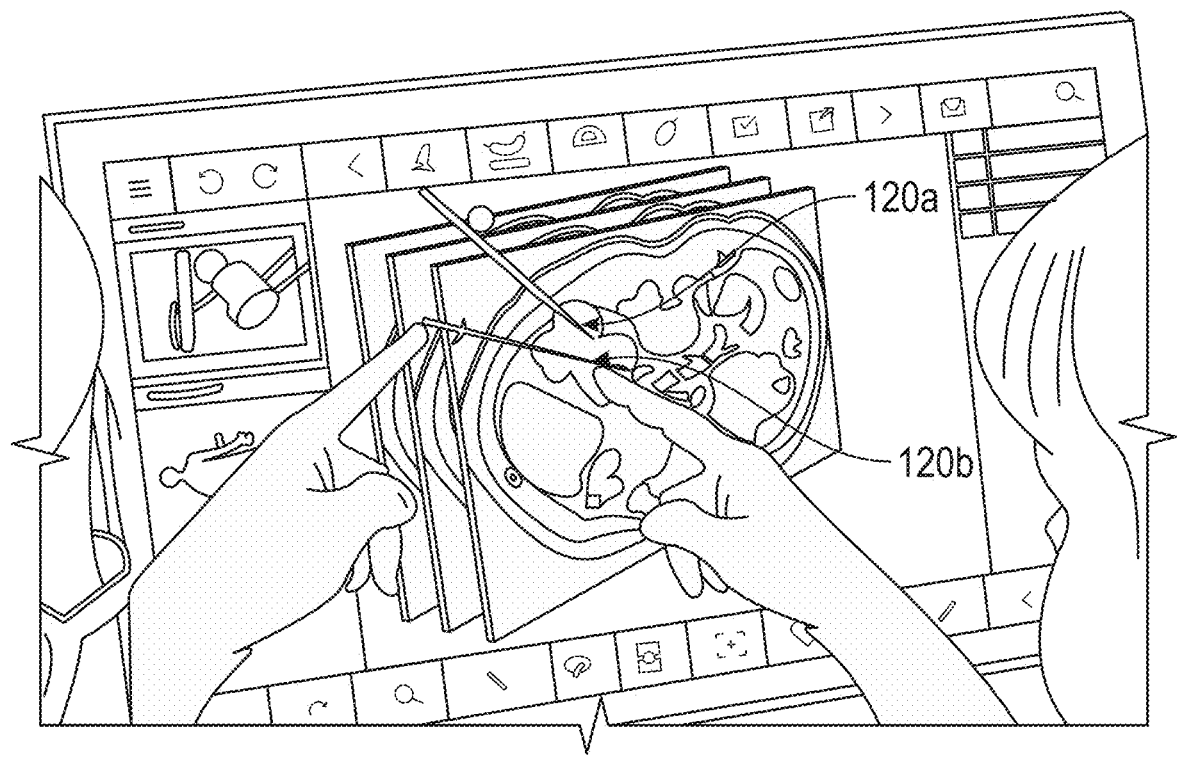

In one or more embodiments, multi-probe or balloon ablation (e.g., as shown in FIGS. 6B-6C) may be used in combination with any feature disclosed herein, including, but not limited to, with a margin map, with a medial axis or center line, with a security or credential check, etc. In one or more embodiments, the size and shape of a biological object, such as a lesion or tumor, may be used to determine whether two or more needles, and two or more probes/balloons, are needed to appropriately ablate a target ablation zone. In one or more embodiments, clinicians may employ a spherical balloon(s) for an ablation zone because it is easy to control. In one or more embodiments, the balloon or balloons may have a different shape, e.g., elliptical or other predetermined shape. Additionally or alternatively, the type of balloon and number of balloons/needles may vary depending on the type of ablation being performed. For example, when performing microwave ablation, RF ablation, laser ablation and/or cryoablation, a spherical balloon may be used or the ablation may require a shape other than spherical. As shown in FIGS.

6B-6C, multi-probe ablation is used with two needles and multiple balloons 120a, 120b to ablate a target ablation zone for a biological object, such as a tumor or lesion. As also shown in FIGS. 6A-6B, the methods disclosed herein may be used to simulate or perform ablation planning when evaluating a biological object or a target/target zone and determining whether to use a two-needle (or more) insertion for ablation.

Additionally, in one or more embodiments, a security check may be included to perform the check in the surgical room prior to the ablation procedure to ensure maximal security and safety. To make the security check convenient for clinicians (who have scrubbed in and are wearing gloves at that point and may not be able to use their hands for performing the security check), iris and/or face recognition may be incorporated. Such iris and/or face recognition based approaches may be preferred to control access to patient data (CT scan for example) and communication with peers. While other forms of security control may be used, forms, such as, but not limited to, typing a password, finger print scan, or other forms that require the use of a clinician's hand(s), may not be preferred because a clinician's hands may be sterilized. Once logged in, clinicians may be able to access patient data and communication with peers.

Figure 7:
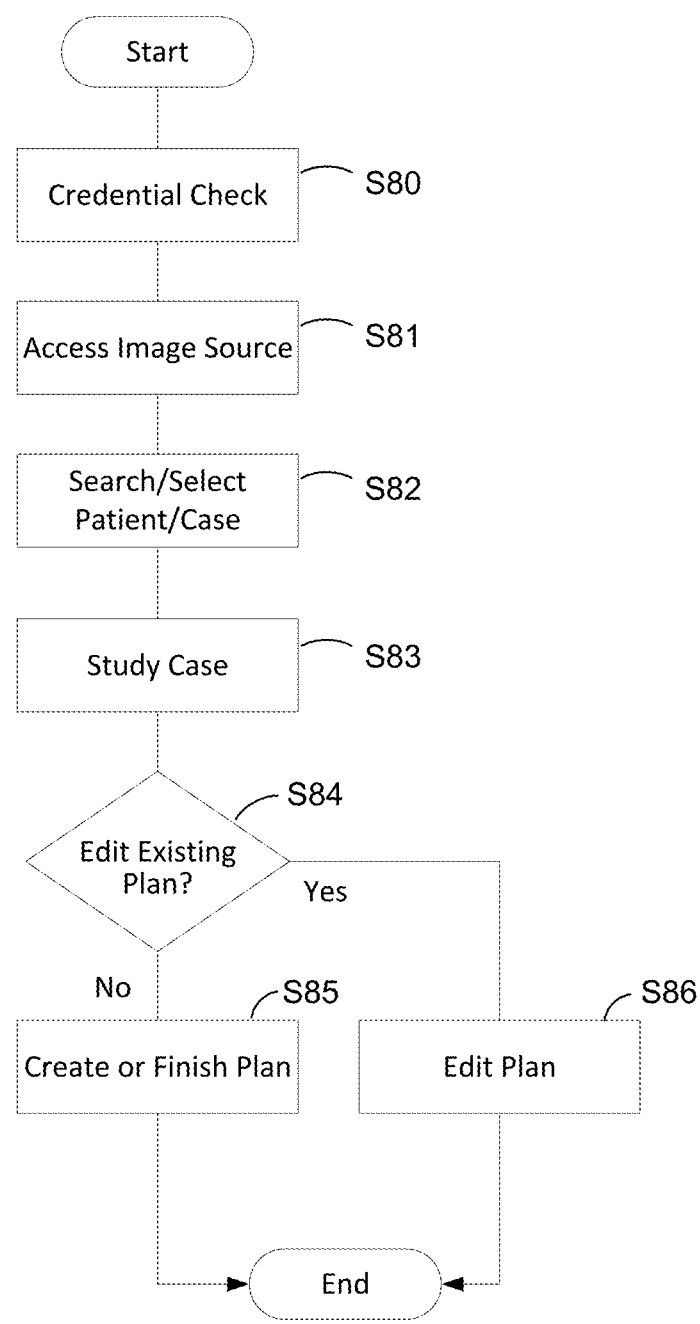
FIG. 7 is a flow chart showing at least another embodiment of a method for performing ablation planning and/or ablation using a security or credential check in accordance with one or more aspects of the present disclosure.

FIG. 7 depicts where this checking step may be employed for access image data to create or edit a plan for any medical procedure, such as ablation, cryotherapy, etc. For example, prior to executing any method disclosed herein for performing ablation planning and/or performance, a credential check (step S80 of FIG. 7) may be performed to make sure that the clinician is permitted to access patient data and communication with other clinicians. Once the clinician passes the credential check (S80), then the clinician has access to the image source (see step S81 of FIG. 7), and may search or select a patient or case file (see step S82 of FIG. 7). Once the patient or case file is retrieved in step S82, the clinician may study the case (see step S83 of FIG. 7), and may determine whether edit(s) to an existing procedure plan (e.g., an ablation plan, a radiotherapy plan, etc.) are required or not (see step S84 in FIG. 7). If "No" edits to an existing plan are needed (e.g., a plan is finished, a plan does not exist, etc.), the clinician may create or finish a plan for the procedure (see step S85 of FIG. 7). If "Yes" at step S84, edits to an existing plan are needed, the clinician may edit the previously created plan (see step S86 of FIG. 7). These steps may be used in addition to any of the aforementioned methods for performing ablation planning and/or ablation performance, for radiotherapy planning and/or performance, for guiding multiple needles or multiple ablation probes, or other procedural methods as may be useful.

In at least one embodiment, the computer 2, 2' operates to control the ablation planning and/or ablation performance and/or probe or needle guidance device(s), system(s) and/or storage medium(s), and may display the scanned image(s) and the procedure plan (e.g., on a monitor or screen such as a display, screen or monitor 1209 as shown in the computer 2 of FIG. 8 and/or the computer 2' of FIG. 9 as further discussed below). The console or processor 2, 2' may be used to control any portions of the system 10 of FIG. 3, for example, including, but not limited to, the ablation device 1, the locator/localizer device 3, the PACS system 4, the CT scanner and console 5, etc. The console 2, 2' may be used to perform any of the aforementioned method(s) or algorithm(s), and may use one or more feature(s) of such method(s) or algorithm(s) in any combination desired by a clinician for a predetermined procedure (e.g., ablation planning and/or performance; needle or probe guidance; a combination thereof; etc.). For example, the processor 2, 2' may load images (e.g., from a scanner or PACS 4) in step S1 of FIGS. 4-5, and may display such images to allow the clinician to visualize the images (e.g., in step S2 of FIGS. 4-5). The computer, such as the console or computer 2, 2', may receive data from a device (e.g., such as the locator device 103, an image scanner 5, a PACS 4, etc.) or a system via a network interface (see e.g., communication interface 1205 and network 1206 as shown in FIG. 8 or Network I/F 1212 as shown in FIG. 9), or the computer, such as the console or computer 2, 2', may obtain a set of imaging conditions using the operation input from the mouse or keyboard (see e.g., the keyboard 1210 as shown in FIG. 8 or the mouse 1211 and/or keyboard 1210 as shown in FIG. 9).

Unless otherwise discussed herein, like numerals indicate like elements. For example, while variations or differences exist between the methods, devices, systems or storage media, such as, but not limited to, the system 10, the methods shown in FIGS. 4-5 and 7, etc., one or more features thereof may be the same or similar to each other, such as, but not limited to, the use of one or more component(s) thereof (e.g., the console 2, the console 2', the ablation device 1, the locator/localizer device 3, the PACS 4, the CT scanner 5, any or all of the components of FIGS. 1A-2C, etc.). Those skilled in the art will appreciate that the method steps disclosed herein may operate in the same or similar fashion to those like-numbered elements of one or more other methods or algorithms as discussed herein. Those skilled in the art will appreciate that alternative embodiments of the system 10, may be used while having other variations as discussed herein for performing one or more methods discussed herein. Likewise, while the console or computer 2 may be used in one or more systems or with one or more methods disclosed herein, one or more other consoles or computers, such as the console or computer 2', may be used additionally or alternatively.

There are many ways to plan for and perform ablation or any other measurement or determination discussed herein, digital as well as analog. In at least one embodiment, a computer, such as the console or computer 2, 2', may be dedicated to control and monitor the devices, systems, methods and/or storage mediums described herein.

Figure 8:
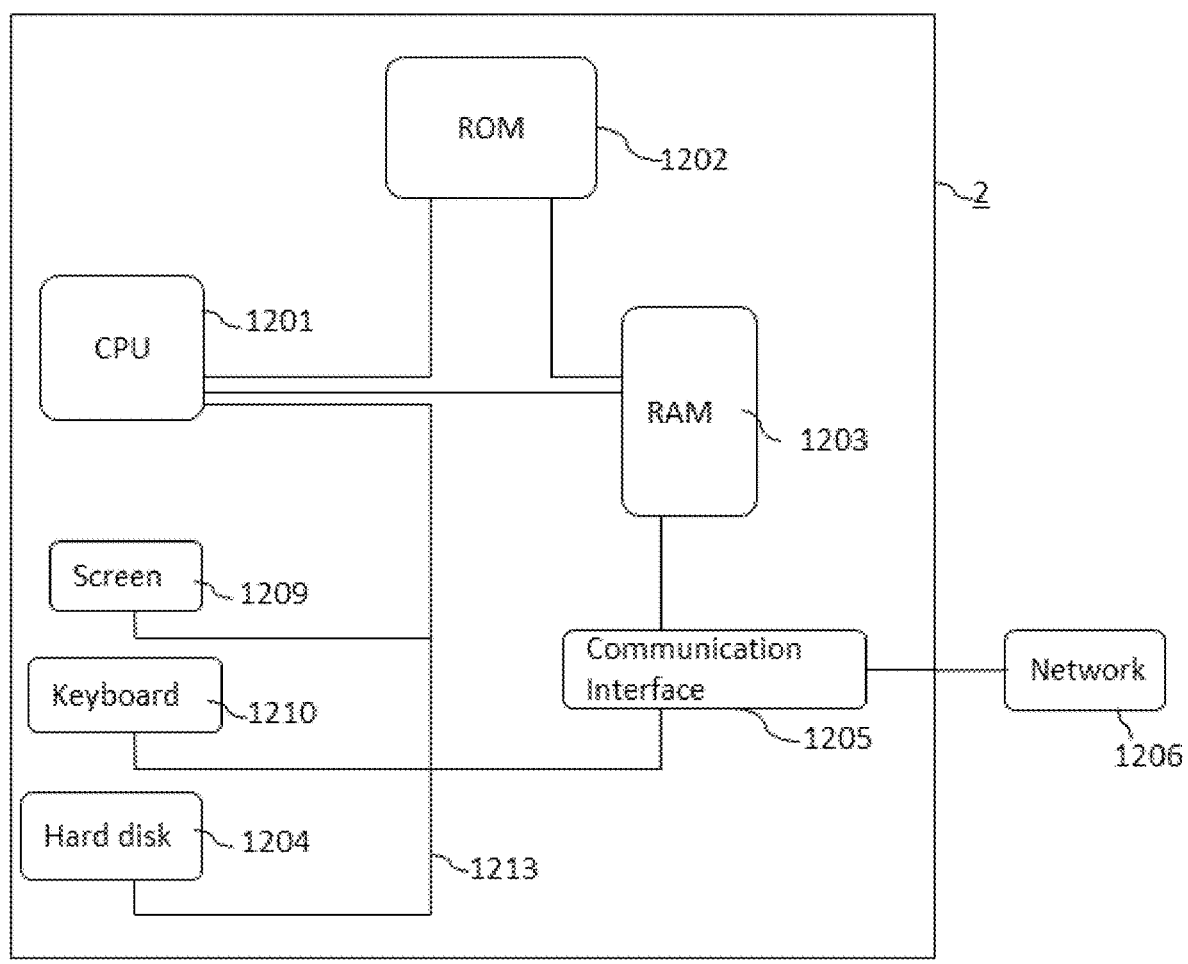
FIG. 8 shows a schematic diagram of an embodiment of a computer that may be used with one or more embodiments of an ablation planning and/or performance method, apparatus or system in accordance with one or more aspects of the present disclosure.
Figure 9:
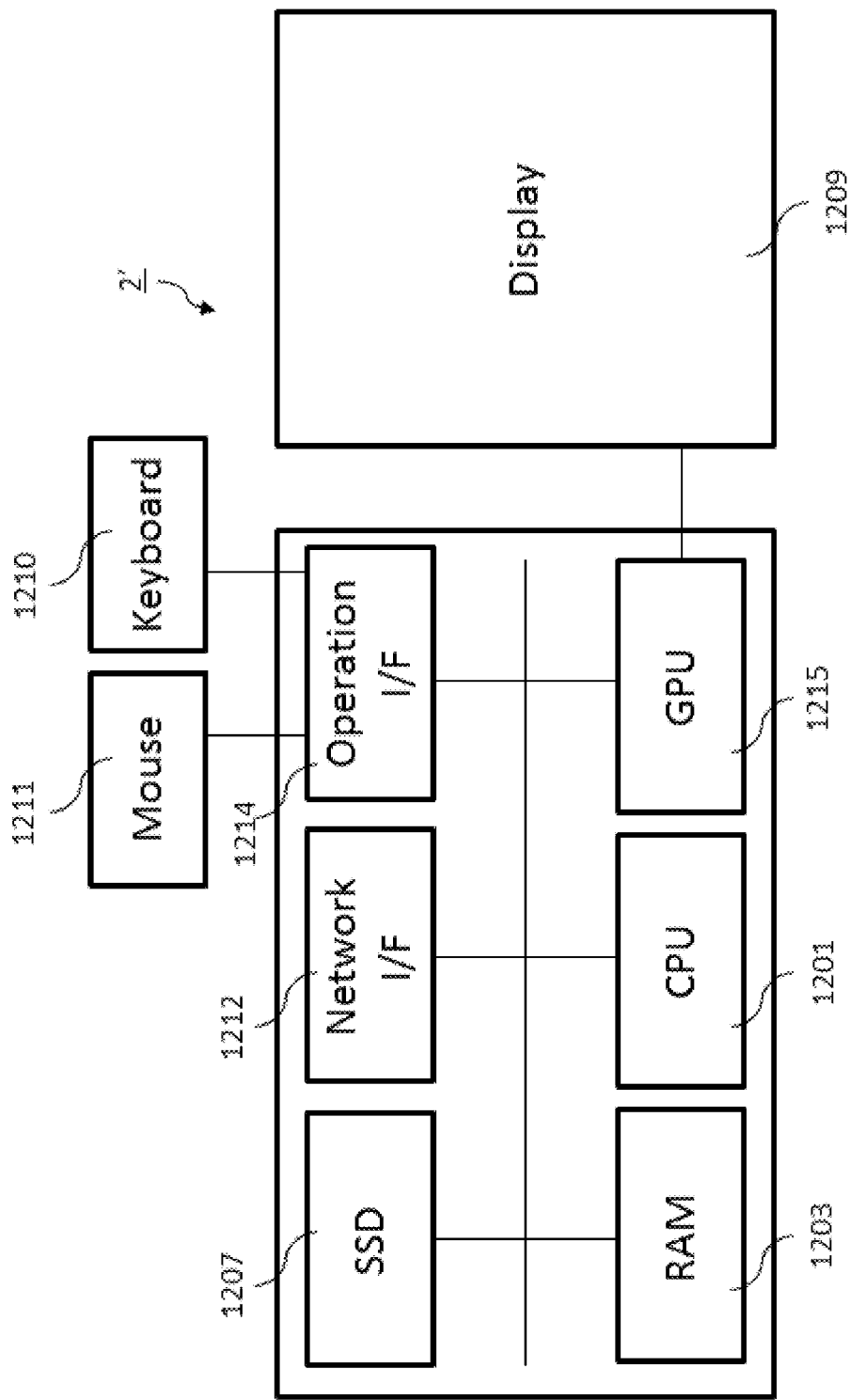
FIG. 9 shows a schematic diagram of another embodiment of a computer that may be used with one or more embodiments of an ablation planning and/or performance

Various components of a computer system 2 (see e.g., the console or computer 2 as shown in FIG. 6A) are provided in FIG. 8. A computer system 2 may include a central processing unit ("CPU") 1201, a ROM 1202, a RAM 1203, a communication interface 1205, a hard disk (and/or other storage device) 1204, a screen (or monitor interface) 1209, a keyboard (or input interface; may also include a mouse or other input device in addition to the keyboard) 1210 and a BUS or other connection lines (e.g., connection line 1213) between one or more of the aforementioned components (e.g., as shown in FIG. 6A). In addition, the computer system 2 may comprise one or more of the aforementioned components. For example, a computer system 2 may include a CPU 1201, a RAM 1203, an input/output (I/O) interface (such as the communication interface 1205) and a bus (which may include one or more lines 1213 as a communication system between components of the computer system 2; in one or more embodiments, the computer system 2 and at least the CPU 1201 thereof may communicate with the one or more aforementioned components of an ablation performance and/or planning and/or needle or probe guidance device or system, such as, but not limited to, the system 10 discussed herein above, via one or more lines 1213), and one or more other computer systems 2 may include one or more combinations of the other aforementioned components. The CPU 1201 is configured to read and perform computer-executable instructions stored in a storage medium. The computer-executable instructions may include those for the performance of the methods and/or calculations described herein. The system 2 may include one or more additional processors in addition to CPU 1201, and such processors, including the CPU 1201, may be used for performing ablation planning and/or performance and/or multiple needle or multiple ablation probe guidance. The system 2 may further include one or more processors connected via a network connection (e.g., via network 1206). The CPU 1201 and any additional processor being used by the system 2 may be located in the same telecom network or in different telecom networks (e.g., performing ablation planning and/or performance technique(s) may be controlled remotely).

The I/O or communication interface 1205 provides communication interfaces to input and output devices, which may include the ablation device 1, the locator/localizer 3, the PACS 4, the CT scanner 5, a microphone, a communication cable and a network (either wired or wireless), a keyboard 1210, a mouse (see e.g., the mouse 1211 as shown in FIG. 9), a touch screen or screen 1209, a light pen and so on. The Monitor interface or screen 1209 provides communication interfaces thereto.

Any methods and/or data of the present disclosure, such as the methods for performing ablation planning and/or performance, radiotherapy, guidance of needle(s) and/or probe(s), or otherwise as discussed herein, may be stored on a computer-readable storage medium. A computer-readable and/or writable storage medium used commonly, such as, but not limited to, one or more of a hard disk (e.g., the hard disk 1204, a magnetic disk, etc.), a flash memory, a CD, an optical disc (e.g., a compact disc ("CD") a digital versatile disc ("DVD"), a Blu-ray™ disc, etc.), a magneto-optical disk, a random-access memory ("RAM") (such as the RAM 1203), a DRAM, a read only memory ("ROM"), a storage of distributed computing systems, a memory card, or the like (e.g., other semiconductor memory, such as, but not limited to, a non-volatile memory card, a solid state drive (SSD) (see SSD 1207 in FIG. 9), SRAM, etc.), an optional combination thereof, a server/database, etc. may be used to cause a processor, such as, the processor or CPU 1201 of the aforementioned computer system 2 to perform the steps of the methods disclosed herein. The computer-readable storage medium may be a non-transitory computer-readable medium, and/or the computer-readable medium may comprise all computer-readable media, with the sole exception being a transitory, propagating signal. The computer-readable storage medium may include media that store information for predetermined or limited or short period(s) of time and/or only in the presence of power, such as, but not limited to Random Access Memory (RAM), register memory, processor cache(s), etc. Embodiment(s) of the present disclosure may also be realized by a computer of a system or apparatus that reads out and executes computer executable instructions (e.g., one or more programs) recorded on a storage medium (which may also be referred to more fully as a "non-transitory computer-readable storage medium") to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s).

In accordance with at least one aspect of the present disclosure, the methods, systems, and computer-readable storage mediums related to the processors, such as, but not limited to, the processor of the aforementioned computer 2, etc., as described above may be achieved utilizing suitable hardware, such as that illustrated in the figures. Functionality of one or more aspects of the present disclosure may be achieved utilizing suitable hardware, such as that illustrated in FIGS. 1A-2C, 3A-3D, 6A, FIG. 8 and/or FIG. 9. Such hardware may be implemented utilizing any of the known technologies, such as standard digital circuitry, any of the known processors that are operable to execute software and/or firmware programs, one or more programmable digital devices or systems, such as programmable read only memories (PROMs), programmable array logic devices (PALs), etc. The CPU 1201 (as shown in FIG. 8 or 9) may also include and/or be made of one or more microprocessors, nanoprocessors, one or more graphics processing units ("GPUs"; also called a visual processing unit ("VPU")), one or more Field Programmable Gate Arrays ("FPGAs"), or other types of processing components (e.g., application specific integrated circuit(s) (ASIC)). Still further, the various aspects of the present disclosure may be implemented by way of software and/or firmware program(s) that may be stored on suitable storage medium (e.g., computer-readable storage medium, hard drive, etc.) or media (such as floppy disk(s), memory chip(s), etc.) for transportability and/or distribution. The computer may include a network of separate computers or separate processors to read out and execute the computer executable instructions. The computer executable instructions may be provided to the computer, for example, from a network or the storage medium.

As aforementioned, hardware structure of an alternative embodiment of a computer or console 2' is shown in FIG. 9. The computer 2' includes a central processing unit (CPU) 1201, a graphical processing unit (GPU) 1215, a random access memory (RAM) 1203, a network interface device 1212, an operation interface 1214 such as a universal serial bus (USB) and a memory such as a hard disk drive or a solid state drive (SSD) 1207. Preferably, the computer or console 2' includes a display 1209. The computer 2' may connect with the ablation device 1, the locator/localizer device 3, the PACS 4, the CT scanner 5, communication devices (e.g., to discuss the procedure with peers, clinicians, etc.) via the operation interface 1214 or the network interface 1212. The operation interface 1214 is connected with an operation unit such as a mouse device 1211, a keyboard 1210 or a touch panel device. The computer 2' may include two or more of each component.

In at least one embodiment, at least one computer program is stored in the SSD 1207, and the CPU 1201 loads the program onto the RAM 1203, and executes the instructions in the program to perform one or more processes described herein, as well as the basic input, output, calculation, memory writing and memory reading processes.

The computer, such as the computer 2, 2', communicates with one or more other system components (e.g., the ablation device 1, the locator/localizer device 3, the PACS 4, the CT scanner 5 or other type of scanner, of system 10 or other device or system being used for ablation planning and/or performance) to perform imaging, planning and/or performance. The monitor or display 1209 displays the plan and performance and/or guidance steps (e.g., in real time), and may display other information about the imaging condition or about an object to be imaged and operated on during the procedure. The monitor 1209 also provides a graphical user interface for a user to operate an ablation planning and/or performance and/or needle guidance or ablation probe guidance device or system (e.g., the system 10). An operation signal is input from the operation unit (e.g., such as, but not limited to, a mouse device 1211, a keyboard 1210, a touch panel device, etc.) into the operation interface 1214 in the computer 2', and corresponding to the operation signal the computer 2' instructs the system (e.g., the system 10) to set or change the imaging, planning and/or performance condition(s), and to start or end any portion of any of the method(s) discussed herein.

The present disclosure and/or one or more components of devices, systems and storage mediums, and/or methods, thereof also may be used in conjunction with any suitable optical assembly including, but not limited to, ablation technology, such as in U.S. Pat. No. 9,867,673; U.S. patent application Ser. Nos. 16/027,093 and 15/836,141; App. No. PCT/US2018/020752; and App. No. PCT/US15/40336, each of which patent(s), patent publication(s) and application(s) are incorporated by reference herein in their entireties.

Although the disclosure herein has been described with reference to particular embodiments, it is to be understood that these embodiments are merely illustrative of the principles and applications of the present disclosure (and are not limited thereto). It is therefore to be understood that numerous modifications may be made to the illustrative embodiments and that other arrangements may be devised without departing from the spirit and scope of the present disclosure. The scope of the following claims is to be accorded the broadest interpretation so as to encompass all such modifications and equivalent structures and functions.

What is claimed is:

1. A system for supporting multi-probe guidance in medical procedures, comprising:
   a medical guidance apparatus comprising:
      a rotatable portion which is rotatable around a first axis;
      an arc guide attached to or integrally formed with the rotatable portion, the arc guide having an arc shape which is centered around a second axis which is perpendicular to the first axis; and
      a probe holder movably mounted on the arc guide,
   wherein the probe holder is rotatable around the second axis by being translated along an arcuate path defined by the arc shape of the arc guide,
   wherein the probe holder is configured to simultaneously guide a plurality of probes into a region of interest of a subject,
   wherein the probe holder includes a plurality of channels formed between the probe holder body and a plurality of doors attached to the probe holder body, and
   wherein a width of each of the plurality of channels is adjustable by controlling a distance between the probe holder body and one or more of the plurality of doors so that the plurality of channels can simultaneously hold therein the plurality of probes having different sizes.

2. The system according to claim 1,
   wherein a top surface of the probe holder is flat and tangent to the curvature of the arc guide such that, among the plurality of channels, each channel is substantially perpendicular to the top surface of the probe holder, and
   wherein the plurality of probes can be inserted into the plurality of channels a same depth to have the tips of the probes at a same distance from the top surface along the insertion trajectory.

3. The system according to claim 1,
   wherein the plurality of channels are equidistant from each other, and
   wherein the plurality of probes are inserted parallel to each other.

4. The system according to claim 1,
   wherein the probe holder holds the plurality of probes parallel to each other and spaced at a predetermined distance from each other, and
   wherein the predetermined distance is below a preset maximum distance to ensure that the plurality of probes form a single uniform ablation zone within the region of interest.

5. The system according to claim 1,
   wherein the probe holder further comprises a plurality of adjusting mechanisms corresponding to the plurality of doors, and
   wherein each pair of a door and an adjusting mechanism is configured to secure to the probe holder one or more than one probe among the plurality of probes.

6. The system according to claim 5,
   wherein each adjusting mechanism is a set screw configured to hold one of the plurality of doors attached to the probe holder body with an adjustable holding force.

7. The system according to claim 1,
   wherein, among the plurality of channels, the probe holder includes a first channel configured to sequentially accept therein the plurality of probes one-by-one, and
   wherein the rotatable portion is configured to rotate around the first axis such that, at each rotational position, the first channel of the probe holder defines a different insertion trajectory for each probe among the plurality of probes.

8. The system according to claim 7,
   wherein the first channel is offset from a center point of the rotatable portion or of the probe holder by a fixed distance such that each probe among the plurality of probes can be inserted sequentially through a different insertion point without colliding at the center point.

9. The system according to claim 7, wherein the first channel is offset by the fixed distance, and the fixed distance is defined as R according to the following equation:

$$R = ((D*N)+S)/2\pi,$$

where D is an average diameter of the plurality of probes to be inserted, N is the maximum number of probes that can be used in a procedure, and S is a safety margin to ensure that there is no probe collision at the center point.

10. The system according to claim 1,
    wherein the plurality of probes are inserted in a conical pattern, or a parallel pattern, or a combination of both the conical pattern and the parallel pattern, and
    wherein the plurality of channels includes a first channel that is offset from a center point of the rotatable portion so as to increase or maximize a number of probes that can be guided with the probe holder to or into the region of interest without colliding at the center point.

11. The system according to claim 1,
    wherein the plurality of channels are formed by a plurality of grooves provided in one or more than one door and in at least one outer surface of the probe holder body.

12. The system according to claim 11,
wherein a first channel is formed by a first groove provided in a first door and a second groove provided in the at least one outer surface of the probe holder body.

13. The system according to claim 12,
wherein both the first groove and the second groove are v-shaped grooves or semi-circle shaped grooves, and
wherein, in the first channel, contact points between a cylindrical probe and the first and second grooves of the first channel are equally distributed around the circumference of the probe.

14. The system according to claim 1, further comprising:
a processor operatively connected to the medical guidance apparatus;
a memory storing program code representing instructions to cause the processor to:
 acquire a scan image of the subject to be treated with multi-probe intervention;
 cause a display device to display the scan image;
 determine at least one region of interest in the scan image of the subject;
 prompt a user to designate a target position within the least one region of interest in the displayed image; and
 guide insertion of the plurality of probes to or into the region of interest based on the designated target position.

15. The system according to claim 1,
wherein, in a case where the probe holder is rotated around the second axis, the probe holder body and each of the plurality of doors move together along the arcuate path defined by the arc shape of the arc guide.

16. The system according to claim 1,
wherein the plurality of doors includes a first door attached to the probe holder body by a first set screw and a second door attached to the probe holder body by a second set screw, and
wherein the width of a first channel and the width of a second channel are simultaneously adjustable by rotating the first set screw to change a distance between the probe holder body and the first door, and the width of a third channel is adjustable by rotating the second set screw to change a distance between the probe holder body and the second door.

17. The system according to claim 1,
wherein the plurality of doors includes a first door attached to the probe holder body by a first set screw and a second door attached to the probe holder body by a second set screw, and
wherein a distance between the first door and the probe holder body, and a distance between the second door and the probe holder body are adjusted separately by respectively rotating the first set screw and the second set screw, so that the plurality of channels can hold therein the plurality of probes having at least two different sizes.

18. The system according to claim 1,
wherein a number of the plurality of doors is smaller than a number of the plurality of channels.

* * * * *